US005773391A

United States Patent [19]
Lawate et al.

[11] Patent Number: 5,773,391
[45] Date of Patent: Jun. 30, 1998

[54] HIGH OLEIC POLYOL ESTERS, COMPOSITIONS AND LUBRICANTS, FUNCTIONAL FLUIDS AND GREASES CONTAINING THE SAME

[75] Inventors: Saurabh S. Lawate, Concord; Kasturi Lal, Willoughby, both of Ohio

[73] Assignee: The Lubrizol Corporation, Wickliffe, Ohio

[21] Appl. No.: 966,769

[22] Filed: Nov. 7, 1997

Related U.S. Application Data

[63] Continuation of Ser. No. 794,105, Feb. 3, 1997, abandoned, which is a continuation of Ser. No. 339,821, Nov. 15, 1994, abandoned.

[51] Int. Cl.$^6$ .................................................. C10M 129/78
[52] U.S. Cl. ......................... 508/257; 508/481; 508/491
[58] Field of Search .................................... 508/257, 481, 508/491

[56] References Cited

U.S. PATENT DOCUMENTS

| | | | |
|---|---|---|---|
| 2,435,159 | 1/1948 | Ross ........................................ | 260/413 |
| 2,457,611 | 12/1948 | Swern ..................................... | 260/409 |
| 2,757,139 | 7/1956 | Matuszak et al. ....................... | 252/56 |
| 3,562,300 | 2/1971 | Chao et al. .............................. | 260/398 |
| 3,790,478 | 2/1974 | Rudston et al. ......................... | 252/4 |
| 4,113,635 | 9/1978 | Sakurai et al. .......................... | 252/49.6 |
| 4,179,454 | 12/1979 | Mehta et al. ............................. | 260/409 |
| 4,226,732 | 10/1980 | Reinhard et al. ....................... | 252/32.5 |
| 4,519,927 | 5/1985 | Seiki ....................................... | 252/49.6 |
| 4,589,990 | 5/1986 | Zehler et al. ........................... | 252/56 S |
| 4,743,402 | 5/1988 | Fick ........................................ | 260/412.2 |
| 4,783,274 | 11/1988 | Jokinen et al. ......................... | 252/32.7 E |
| 4,785,095 | 11/1988 | Salomon .................................. | 544/38 |
| 4,978,465 | 12/1990 | Sturwold ................................. | 252/56 R |
| 5,145,593 | 9/1992 | Takashima .............................. | 252/56 R |
| 5,260,077 | 11/1993 | Carrick et al. .......................... | 426/73 |
| 5,308,521 | 5/1994 | Pavilon et al. .......................... | 252/49.6 |
| 5,399,275 | 3/1995 | Lange et al. ............................ | 252/56 R |
| 5,427,704 | 6/1995 | Lawate .................................... | 252/56 R |

*Primary Examiner*—Jacqueline V. Howard
*Attorney, Agent, or Firm*—James L. Cordek; Joseph P. Fischer; William J. Connors

[57] ABSTRACT

A polyol ester is described which is derived from:

(A) an aliphatic or alicyclic polyol; and
(B) an aliphatic monocarboxylic mixture derived from a natural vegetable oil, said acid mixture comprising at least about 72% by weight of oleic acid.

The invention also relates to compositions comprising the polyol esters and at least one antioxidant, and lubricating oil compositions comprising an oil of lubricating viscosity and the polyol esters of the invention. Lubricating oil compositions comprising polyol esters of the invention, at least one antioxidant, and an oil of lubricating viscosity also are described and are particularly useful.

29 Claims, No Drawings

HIGH OLEIC POLYOL ESTERS, COMPOSITIONS AND LUBRICANTS, FUNCTIONAL FLUIDS AND GREASES CONTAINING THE SAME

This is a continuation of applications Ser. No. 08/794,105 filed on Feb. 3, 1997, now abandoned, which is a continuation of Ser. No. 08/339,821 filed on Nov. 15, 1994, now abandoned.

FIELD OF THE INVENTION

The invention relates to polyol esters, and more particularly, to polyol esters derived from polyols and aliphatic monocarboxylic acid mixtures derived from natural vegetable oils wherein the acid mixtures comprise at least about 72% by weight of oleic acid. The polyol esters are useful in a variety of applications including lubricants, functional fluids and greases.

BACKGROUND OF THE INVENTION

Synthetic esters are commonly used as lubricating base fluids. Many of the synthetic esters are polyol esters. Polyol esters are produced by the reaction of polyols such as pentaerythritol and trimethylolpropane (TMP) with various fatty acids such as the fatty acids obtained by the saponification of animal oils such as beef tallow, lard, mutton tallow; fatty acids produced from vegetable oils such as sunflower, rapeseed oil, castor oil, olive oil, palm kernel oil, coconut oil, etc.; and straight chain fatty acids such as lauric acid, myristic acid, palmitic acid, stearic acid, behenic acid and olefinic fatty acids such as oleic acid. Esters useful as synthetic oils include those made from fatty acids and polyols such as neopentyl glycol, trimethylol-propane, pentaerythritol, and polyol ethers such as dipentaerythritol, ditrimethylol propane, etc. Trimethylolpropanoyl trioleate is a commonly used synthetic ester of the polyol type which is sold by various manufacturers. The commercial TMP trioleate has good low temperature properties but has poor oxidative stability.

The present invention is concerned primarily with synthetic esters derived from aliphatic or alicyclic polyols and aliphatic monocarboxylic acid mixtures derived from natural vegetable oils, and, in particular, those natural vegetable oils which are high in oleic acid content.

Vegetable oils such as sunflower oil, rapeseed oil, safflower oil, peanut oil, soybean oil and corn oil comprise a mixture of fatty acids including oleic, linoleic and linolenic. For example, sunflower oil is comprised primarily of palmitic, stearic, oleic and linoleic acids. In recent years, an increase in the oleic acid content, based on the total fatty acid content of various vegetable oils has been obtained by modifying the plants through breeding (hybridization), mutation or various genetic modifications. A history of the development of sunflower hybrids is found in U.S. Pat. No. 4,743,402 (Fick). The Fick patent also describes and claims a sunflower seed which has an oleic acid content of about 80% or greater, relative to the total fatty acid content of the seed. Oleic acid contents of up to about 94% are reported.

SUMMARY OF THE INVENTION

A polyol ester is described which is derived from: (A) an aliphatic or alicyclic polyol; and (B) an aliphatic monocarboxylic mixture derived from a natural vegetable oil, said acid mixture comprising at least about 72% by weight of oleic acid. The invention also relates to compositions comprising the polyol esters and at least one antioxidant, and lubricating oil compositions comprising an oil of lubricating viscosity and the polyol esters of the invention. Lubricating oil compositions comprising polyol esters of the invention, at least one antioxidant, and an oil of lubricating viscosity also are described and are particularly useful.

DESCRIPTION OF THE PREFERRED EMBODIMENTS

In order to provide an understanding of a number of terms and phrases used in this specification and claims, the following definitions are provided.

The term "oleic acid" refers to cis-9,10-octadecenoic acid.

The term "natural vegetable oils" refers to vegetable oils obtained from the seeds and/or fruits of plants which are grown naturally although the plants have been modified through breeding (hybridization), mutation or various genetic modifications. In particular the plants have been modified to produce seeds wherein the oil obtained from the seeds contains oleic acid in an amount of at least 72% by weight of the acids recovered from the oil. The oil may be recovered from the seeds and/or fruits by techniques known to those skilled in the art.

The content of the various fatty acids such as oleic, linoleic and linolenic, contained in the mixtures of fatty acids derived from the natural vegetable oils is commonly expressed as a percentage of the total fatty acid fraction of the oil. Dimensionless ratios of either linoleic acid or linolenic acid to oleic acid in the monocarboxylic acid mixtures derived from natural vegetable oils are calculated by dividing the weight or the percentage of either the linoleic acid or the linoleic acid by the weight or percentage of oleic acid present in the mixture, as applicable.

The term "hydrocarbyl" includes hydrocarbon, as well as substantially hydrocarbon, groups. Substantially hydrocarbon describes groups which contain non-hydrocarbon substituents which do not alter the predominately hydrocarbon nature of the group.

Examples of hydrocarbyl groups include the following:

(1) hydrocarbon substituents, that is, aliphatic (e.g., alky, alkenyl or alkynyl), alicyclic (e.g., cycloalkyl, cycloalkenyl) substituents, aromatic-, aliphatic- and alicyclic-substituted aromatic substituents and the like as well as cyclic substituents wherein the ring is completed through another portion of the molecule (that is, for example, any two indicated substituents may together form an alicyclic radical);

(2) substituted hydrocarbon substituents, that is, those substituents containing non-hydrocarbon groups which, in the context of this invention, do not alter the predominantly hydrocarbon substituent; those skilled in the art will be aware of such groups (e.g., halo (especially chloro and fluoro), hydroxy, alkoxy, keto, mercapto, alkylmercapto, nitro, nitroso, sulfoxy, etc.);

(3) hetero substituents, that is, substituents which will, while having a predominantly hydrocarbon character within the context of this invention, contain other than carbon present in a ring or chain otherwise composed of carbon atoms. Suitable heteroatoms will be apparent to those of ordinary skill in the art and include, for example, sulfur, oxygen, nitrogen and such substituents as, e.g., pyridyl, furyl, thienyl, imidazolyl, etc. In general, no more than about 2, preferably no more than one, non-hydrocarbon substituent will be present for every 10 carbon atoms in the hydrocarbyl group. Often, there will be no such non-hydrocarbon substituents in the hydrocarbyl group, and the hydrocarbyl group is purely a hydrocarbon group.

Throughout the specification and claims, all references to parts and percentages are to be understood as being by weight, temperatures are in degrees Centigrade and pressure is at or near atmospheric pressure unless otherwise indicated.

Polyol Esters

The polyol esters of the present invention are derived from (A) an aliphatic or alicyclic polyol; and
(B) an aliphatic monocarboxylic acid mixture derived from a natural vegetable oil, said acid mixture comprising at least about 72% by weight of oleic acid.

(A) Polyol

The aliphatic polyols which may be utilized in the preparation of the polyol esters of the present invention include aliphatic polyols containing from 2 to about 20 carbon atoms and from 2 to about 10 hydroxyl groups. In one embodiment, the aliphatic. polyol may be characterized by the formula wherein R is a hydrocarbyl group and n is at least 2. The hydrocarbyl group also may contain one or more nitrogen or oxygen atoms. The polyol may contain one or more oxyalkylene groups, and, thus, the polyhydroxy compounds include compounds such as polyether polyols.

In another embodiment, the polyols used in the invention may be characterized by the formula

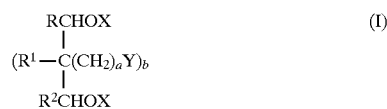  (I)

wherein each X independently is hydrogen, a hydroxyhydrocarbyl or a hydroxyhydrocarbyloxyhydrocarbyl group, R, $R^1$ and $R^2$ are each independently hydrogen, hydrocarbyl, hydroxyhydrocarbyl or alkoxyhydrocarbyl groups, a and b are each independently integers from 0 to about 6, and Y is hydrogen or hydroxyl, or b is 1 and Y is

As noted, X is hydrogen, a hydroxyhydrocarbyl group or a hydroxyhydrocarbyloxyhydrocarbyl group. The hydroxyhydrocarbyl groups may be derived from the hydroxy group (X is hydrogen) by reaction of an alkylene oxide. Examples of alkylene oxides include ethylene oxide, propylene oxide, etc. X also may be a hydroxyhydrocarbyloxyhydrocarbyl group and such groups are obtained by reacting a hydroxyl group with at least one equivalent of an alkylene oxide such as ethylene oxide, propylene oxide, etc.

The R, $R^1$ and $R^2$ groups in the polyol of Formula I are each independently hydrogen, hydrocarbyl, hydroxyhydrocarbyl or alkoxyhydrocarbyl groups. The hydrocarbyl, hydroxyhydrocarbyl and alkoxyhydrocarbyl groups may contain from about 1 to about 10 carbon atoms.

In Formula I, a and b are each independently integers of from 0 to about 6, and in one preferred embodiment, a and b are each independently 0 or 1. In another embodiment, R and $R^2$ are hydrogen, $R^1$ is hydrogen or an alkyl group, X is hydrogen, Y is a hydroxyl group and a is 0. In a further embodiment, R and $R^2$ are each independently hydrogen or alkyl groups and b is 0.

In another embodiment, X is independently hydrogen, hydroxyhydrocarbyl or a hydroxyhydrocarbyloxyhydrocarbyl group, R, $R^1$ and $R^2$ are each independently hydrogen, hydrocarbyl, hydroxyhydrocarbyl or alkoxyhydrocarbyl groups, a is an integer of from 0 to about 6, b is 1 and Y is

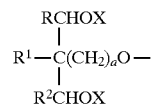

Specific examples of polyols which are represented by Formula I include, ethylene glycol; diethylene glycol; triethylene glycol; glycerol; 1,2-propanediol; 1,3-propanediol; 1,2-butanediol; 1,3-butanediol; 1,4-butenediol; 2,3-butanediol; 2-ethyl-1,3-propanediol; 2-ethyl-2-butyl-1,3-propanediol; neopentyl-glycol; 2,2,4-trimethyl-1,3-pentanediol; trimethylolpropane; pentaerythritol; ditrimethyolpropane; dipentaerythritol; sorbitol; hexaglycerol; etc.

In the polyols of Formula I, X may be hydroxyhydrocarbyl or hydroxyhydrocarbyloxyhydrocarbyl groups, and these compounds can be obtained, for example, by reacting a compound of Formula I where X=H, with one or more moles of an alkylene oxide such as ethylene oxide or propylene oxide, or mixtures of the two oxides. A number of such polyols are commercially available from Perstop Polyols. For example, Perstop Polyol TP 30 is an ethoxylated trimethylolpropane (TMP) with a molar ratio of 1:3 (TMP:ethylene oxide). All of the hydroxyl groups are reported to be primary. Perstop Polyol PP 30 is an ethoxylated pentaerythritol with a molar ratio of 1:3 (pentaerythritol:ethylene oxide). The hydroxy groups are all primary. Perstop Polyol TS 30 is a propoxylated TMP and Perstop Polyol PS 50 is a propoxylated pentaerythritol.

In another embodiment, the polyol (A) is an aliphatic polyol characterized by the formula

  (II)

wherein $R^3$ is an alkyl group containing from 1 to about 6 carbon atoms or a hydroxymethyl group, Y is hydrogen or

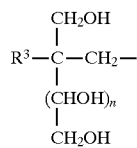

and n is an integer of from 0 to about 6. In one embodiment, n is 0 and in another embodiment, $R^3$ is an alkyl group containing from 1 to 6 carbon atoms and n is 0. Examples of such alkyl groups include methyl, ethyl, propyl, butyl, isobutyl, secondary butyl, n-hexyl, 2-methylpentyl, etc. In another embodiment, $R^3$ is an ethyl group or a hydroxymethyl group and n is 0. Specific examples of polyols represented by Formula II include trimethylol propane, pentaerythritol, ditrimethylolpropane and dipentaerythritol.

The polyol (A) used to form the polyesters of the present invention also may be an alicyclic polyol. The alicyclic polyols may contain from 5 to 10 carbon atoms and from 5 to 10 hydroxyl groups. Examples of useful alicyclic polyols include 1,2-cyclohexanediol; 1,4-cyclohexanediol; and inositol. Other natural polyols such as glucose, galactose, mannose, sorbose and talose can also be used.

(B) Aliphatic Monocarboxylic Acid Mixtures.

The polyol esters of the present invention are obtained by reacting an aliphatic or alicyclic polyol as described above with (B) an aliphatic monocarboxylic acid mixture derived from a natural vegetable oil, said acid mixture comprising at least about 72% by weight of oleic acid. The aliphatic monocarboxylic acid mixture may be derived from any natural vegetable oil provided that the acid mixture thus obtained comprises at least about 72% by weight of oleic acid. Examples of such oils include sunflower oil, rapeseed oil, canola oil, olive oil, safflower oil, peanut oil, corn oil and soybean oil. Canola oil is a variety of rapeseed oil containing less than 1% erucic acid. Sunflower oil is a particularly preferred oil from which the desired aliphatic monocarboxylic acid mixtures can be obtained. As mentioned, the aliphatic monocarboxylic acid mixtures obtained from such natural vegetable oils should contain at least 72% by weight of oleic acid. In other embodiments, the acid mixtures comprise at least 75%, more often at least about 78% or at least about 85% or at least about 90% by weight of oleic acid. The amount of oleic acid in the mixtures may be as high as about 98% by weight. To the extent possible, the amount of linoleic and linolenic acids present in aliphatic monocarboxylic acid mixtures should be at a minimum, and as the oleic acid content of the acid increases, the content of the linoleic and linolenic acids decreases.

The preferred weight ratios of linoleic to oleic acid in the carboxylic acid mixtures useful in the present invention are summarized in the following Table I.

TABLE I

| Oleic Acid Content (% w) | Linoleic/Oleic Ratio |
|---|---|
| 72 | <0.22 |
| 75 | <0.20 |
| 78 | <0.18 |
| 80 | <0.16 |
| 85 | <0.12 |
| 90 | <0.08 |

The amount of linolenic acid present in the carboxylic acid mixtures should generally be less than 5% by weight of the acid mixture. Thus, the acid mixture used to prepare polyol esters useful in the present invention comprise at least about 72% by weight of oleic acid and less than 5% by weight of linolenic acid. More preferred are carboxylic acid mixtures containing less than 4% and even less than 3% by weight of linolenic acid.

U.S. Pat. Nos. 4,627,192 and 4,743,402 describe procedures for preparing high oleic sunflower oils, and the disclosures of these patents are hereby incorporated by reference. Other vegetable oils which can be utilized in the invention are high oleic safflower oil, high oleic peanut oil, high oleic corn oil, high oleic rapeseed oil, canola oil, high oleic soybean oil, high oleic cottonseed oil, high oleic lesquerella oil, and high oleic palm oil provided that the fatty acid mixtures recovered from these oils contain the desired 72% or more of oleic acid. A preferred high oleic vegetable oil is high oleic sunflower oil obtained from *Helianthus sp.* This product is available from SVO Enterprises, Eastlake, Ohio as Sunyl® high oleic sunflower oil. Sunyl® 80 oil is a high oleic triglyceride wherein the acid moieties comprise from about 77% to about 81% of oleic acid. Sunyl® 90 oil is another high oleic triglyceride wherein the acid moieties comprise from about 86% to 92% oleic acid. Another useful high oleic vegetable oil is high oleic rapeseed oil obtained from *Brassica campestris* or *Brassica napus,* also available from SVO Enterprises as RS high oleic rapeseed oil. RS 80 signifies a rapeseed oil wherein the acid moieties comprise about 80% of oleic acid.

The high oleic acid mixtures can be recovered from the high oleic triglyceride oils described above by techniques well known to those skilled in the art according to the following reactions.

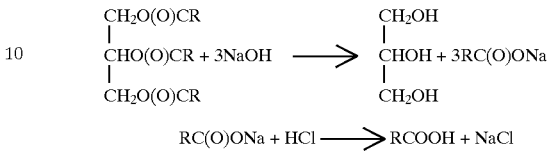

In the above formula, RC(O)OH represents an acid mixture in which the oleic acid content is at least 72% by weight. The acid mixture also can be recovered directly from the high oleic triglyceride oils by steam splitting in autoclaves at medium or low pressures, generally with catalysts such as zinc, magnesium or calcium oxides. High oleic acid mixtures can also be derived from high oleic glyceride oils by fat splitting through the use of lipolytic enzymes. Procedures for steam splitting and enzymatic splitting are described in more detail in *Bailey's Industrial Oil and Fat Products,* Daniel Swern, Editor, Vol. 2, Fourth Edition, John Wiley & Sons, New York (1979), pp. 107–111.

The polyol esters of the present invention are prepared by reaction of any of the above-described aliphatic or alicyclic polyols with the above-described aliphatic monocarboxylic acid mixtures derived from natural vegetable oil wherein the acid mixture is comprised of at least about 72% by weight of oleic acid. Since it is generally preferred that all of the hydroxy groups of the aliphatic or alicyclic polyol are esterified with the aliphatic monocarboxylic acid mixture, a sufficient amount of the acid mixture must be utilized in the reaction to effect esterification of the hydroxyl groups. Thus, for example, one equivalent of ethylene glycol is reacted with at least about two equivalents of the aliphatic monocarboxylic acid mixtures described above; one equivalent of trimethylolpropane is reacted with at least about three equivalents of the aliphatic monocarboxylic acid mixtures; one equivalent of ditrimethylolpropane is reacted with at least about five equivalents of the aliphatic monocarboxylic acid mixture; one equivalent of pentaerythritol is reacted with at least about four equivalents of the aliphatic monocarboxylic acid mixture; etc.

The reaction can be effected utilizing a Bronstead or Lewis acid catalyst at temperatures in the vicinity of 75° C. to 200° C., and more often in the vicinity of about 150° C. The reaction can also be effected in the absence of a catalyst at temperatures above about 200° C. The formation of esters by reaction of a polyol and monocarboxylic acids is a reversible process which can be made to proceed to completion by removing water from the reaction mixture as the water is formed. If the polyol ester is to be formed by transesterification of a lower molecular weight carboxylic acid ester, the reaction can be forced to completion by removal of water, or the low molecular weight alcohol or acid formed as a result of the transesterification reaction. The esterification reaction can be catalyzed by either organic acids or inorganic acids. Examples of inorganic acids include sulfuric acid and acidified clays. A variety of organic acids can be utilized including methane sulfonic acid, benzenesulfonic acid, toluenesulfonic acid, and acidic resins such as Amberlyst 15, etc. The reaction is completed when water or low molecular weight alcohol or acid is no longer formed, and such completion is indicated when water, or low molecular weight alcohol or acid can no longer be removed by distillation. Completion of the reaction can also be followed by determination of the acid number of the reaction mixture. Generally, the reaction is complete in about 5 to about 15 or more hours, and more often the reaction is essentially complete after about 5 to 10 hours of heating at 150° C. Although not required, the reaction may be conducted in the presence of a solvent. Examples of solvents include aromatic hydrocarbon solvents such as xylene, toluene, naphtha, mineral oil, and the like.

When the reaction is complete, the reaction product can be refined by treating with sodium hydroxide with stirring. This procedure is exothermic and the temperature is allowed to rise to about 60° C. The mixture. is then centrifuged, and the supernatant liquid is decanted and recovered as the product. The product can then be washed with water, and the aqueous layer which forms is discarded. The washed product may then be bleached with an acidic material such as an acidified clay (e.g., Super Filtrol, a sulfuric acid treated diatomaceous earth) and filtered. The filtrate is the desired product.

The following examples illustrate the preparation of polyol esters in accordance with the present invention.

EXAMPLE 1

A mixture of 445.3 grams (1.58 moles) of a carboxylic acid mixture derived from Sunyl® 80 oil, 67 grams (0.5 mole) of trimethylol propane and 500 ml. of xylene is prepared with stirring, and 1.28 grams of methane sulfonic acid are added. The mixture is heated under a blanket of nitrogen pressure for a total of 14 hours. Initially, the temperature is maintained at about 100° C. as 25 ml. of water are removed during the first 5.5 hours. After about 7 hours, the temperature begins to rise to about 150° C., and additional water is removed. After 14 hours of heating, the xylene is removed from the reaction mixture under reduced pressure. The residue is a dark, orange-brown liquid. This residue is refined by treatment with 145 ml. of 20° Baume sodium hydroxide. The mixture is centrifuged, and the product (420 grams) is recovered by decantation. This product is washed with 90 ml. of water at 60° C. for 15 minutes and centrifuged. The product is then bleached by treatment with Filtrol grade F160 at 90° C. and filtered under vacuum. The filtrate is the desired product.

EXAMPLE 2

A mixture of 1734 grams (6.15 moles) of an oleic acid mixture obtained from Sunyl 90 oil and 268 grams (2.0 moles) of trimethylolpropane is prepared with stirring, and 2 grams of methanesulfonic acid are added. The mixture is heated to a temperature of 155° C. to 160° C., and water is removed from the reaction mixture. About 78 ml. of water are collected in about six hours. Heating is continued for an additional five hours. A total of 90 ml of water is collected. The product of the reaction is refined with 70 ml. of 20° Baume sodium hydroxide and centrifuged. The supernatant liquid is separated, washed with water and thereafter bleached with Filtrol grade 105 at 90° C. under 2.5 Torr Hg. A yield of 1610 grams of the desired triester is obtained representing about a 92% yield. The product is a clear, light-yellow fluid having a kinematic viscosity (ASTM D 2270) at 40° C. of 46.95 cSt, and at 100° C. of 9.51 cSt, and a viscosity index of 194.

EXAMPLE 3

A mixture of 804 grams (6 moles) of trimethylolpropane and 5343.6 (18.94 moles) grams of an oleic acid mixture containing 80% oleic acid is prepared, and 6 grams of methanesulfonic acid are added with stirring. The mixture is heated to 150° C. with nitrogen bubbling and water is collected and removed from the reaction mixture. The reaction is about 96–97% complete after eight hours based upon the amount of recovered water. Heating is continued for a total of 14 hours. After cooling, 201 ml. of 20° Baume sodium hydroxide are added to refine the product. The supernatant liquid is removed, washed with water and stripped by heating at 60° C. and 2 mm. Hg. The product is then bleached with Filtrol grade 105 at 80° C. for 30 minutes under 2 mm. Hg. The mixture is filtered, and the filtrate is the desired product obtained in about 85% yield. The triester prepared in this manner is characterized as having a kinematic viscosity at 40° C. of 48.4 cSt, and at 100° C. of 10.04 cSt, and a viscosity index of 201.

EXAMPLE 4

A mixture of 580 grams (2.056 moles) of an oleic acid mixture derived from sunflower oil and containing 87% by weight of oleic acid, 68 grams (0.5 mole) of pentaerythritol and 500 ml. of xylene is prepared, and 2.74 grams of methane sulfonic acid are added to the mixture with stirring. The mixture is then heated to about 160° C. and maintained at this temperature while removing water from the reaction mixture. Most of the water is collected within three hours, and additional water is collected in the next three hours. After standing overnight, the mixture is refined by adding 44 ml. of 20° Baume sodium hydroxide. The mixture is stirred for 15 minutes as the temperature reaches 60° C. The mixture is centrifuged and the top layer is removed and washed with water and heated to 60° C. and again centrifuged. The water is removed, and the product is bleached by mixing with 2% by weight of bleaching clay and heating to 80° C. for 45 minutes under vacuum. Before addition of the clay, any residual water was removed by distillation. The mixture of product and bleaching clay is then filtered, and the filtrate is the desired product and characterized as having a kinematic viscosity (D 2270) at 40° C. of 60 cSt and at 100° C. of 12.24 cSt. The tetraester has a viscosity index of 191 and is obtained in 77.4% yield.

EXAMPLE 5

The general procedure of Example 1 is repeated except that the trimethylolpropane is replaced by an equivalent molar amount of ethylene glycol, and the ethylene glycol is esterified with 2 moles of the oleic acid per mole of ethylene glycol.

The polyol esters prepared in accordance with the present invention from aliphatic monocarboxylic acid mixtures wherein the acids in the mixtures comprise at least 72% by weight of oleic acid exhibit significantly improved oxidation stability when combined with at least one antioxidant. The improvement in oxidative stability of polyol esters prepared from oleic acid mixtures containing less than 72% by weight of oleic acid is significantly less than the improvement obtained with the polyol esters of the present invention.

Antioxidants.

A wide variety of antioxidant compositions can be used in combination with the polyol esters of the invention. Examples of various types of antioxidants which can be used in combination with the polyol esters include sulfur-containing compositions, aromatic amines including alkylated aromatic amines, phenols, oil-soluble transition metal containing compounds, etc. More particularly, the antioxidants useful in the present invention may be selected from phenolics, aromatic amines, phenothiazines, dithiophosphates, dithiocarbamates, sulfides, sulfurized olefins, sulfurized oils including vegetable oils, sulfurized fatty acids or esters, sulfurized Diels-Alder adducts, and tocopherols.

Small amounts of antioxidants interact with the polyol esters of the present invention to provide highly stable polyol esters. Generally, the polyol esters can be stabilized with up to 5% by weight, based on the weight of the polyester, of one or more antioxidant, and more often, amounts of 3% or less of an antioxidant or mixture of antioxidants is effective in significantly improving the stability of the polyol esters.

Oils which may be sulfurized to provide antioxidants are natural or synthetic oils including lard oil, carboxylic acid esters derived from aliphatic alcohols and fatty acids or aliphatic carboxylic acids (e.g., myristyl oleate and oleyl oleate) jojoba oil, sperm whale oil, synthetic sperm whale oil substitutes and synthetic unsaturated esters or glycerides.

Fatty acids generally contain from about 8 to about 30 carbon atoms. The unsaturated fatty acids generally contained in the naturally occurring vegetable or animal fats and such acids include palmitoleic acid, oleic acid, linoleic acid, linolenic acid, and erucic acid. The fatty acids may comprise mixtures of acids, such as those obtained from naturally occurring animal and vegetable oils, including beef tallow, depot fat, lard oil, tall oil, peanut oil, corn oil, safflower oil, sesame oil, poppy-seed oil, soybean oil, cottonseed oil, sunflower seed oil, or wheat germ oil. Tall oil is a mixture of rosin acids, mainly abietic acid, and unsaturated fatty acids, mainly oleic and linoleic acids. Tall oil is a by-product of the sulfate process for the manufacture of wood pulp.

The fatty acid esters also may be prepared from aliphatic olefinic acids of the type described above by reaction with any of the above-described alcohols and polyols. Examples of aliphatic alcohols include monohydric alcohols such as methanol, ethanol; 1 or 2 propanol, n-, iso-, sec-, or tert-butyl alcohol, etc.; and polyhydric alcohols including ethylene glycol, propylene glycol, trimethylene glycol, neopentyl glycol, glycerol, etc.

The olefinic compounds which may be sulfurized are diverse in nature. They contain at least one olefinic double bond, which is defined as a non-aromatic double bond; that is, one connecting two aliphatic carbon atoms. In its broadest sense, the olefin may be defined by the formula $R^{*1}R^{*2}C=CR^{*3}R^{*4}$, wherein each of $R^{*1}$, $R^{*2}$, $R^{*3}$ and $R^{*4}$ is hydrogen or an organic group. In general, the R* groups in the above formula which are not hydrogen may be satisfied by such groups as $-C(R^{*5})_3$, $-COOR^{*5}$, $-CON(R^{*5})_2$, $-COON(R^{*5})_4$, $-COOM$, $-CN$, $-X$, $-YR^{*5}$ or $-Ar$, wherein:

each $R^{*5}$ is independently hydrogen, alkyl, alkenyl, aryl, substituted alkyl, substituted alkenyl or substituted aryl, with the proviso that any two $R^{*5}$ groups can be alkylene or substituted alkylene whereby a ring of up to about 12 carbon atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl group of up to about 12 carbon atoms.

Any two of $R^{*1}$, $R^{*2}$, $R^{*3}$ and $R^{*4}$ may also together form an alkylene or substituted alkylene group; i.e., the olefinic compound may be alicyclic.

The olefinic compound is usually one in which each R group which is not hydrogen is independently alkyl, alkenyl or aryl group. Monoolefinic and diolefinic compounds, particularly the former, are preferred, and especially terminal monoolefinic hydrocarbons; that is, those compounds in which $R^{*3}$ and $R^{*4}$ are hydrogen and $R^{*1}$ and $R^{*2}$ are alkyl or aryl, especially alkyl (that is, the olefin is aliphatic) having 1 to about 30, preferably 1 to about 16, more preferably 1 to about 8, and more preferably 1 to about 4 carbon atoms. Olefinic compounds having about 3 to 30 and especially about 3 to 16 (most often less than 9) carbon atoms are particularly desirable.

Isobutene, propylene and their dimers, trimers and tetramers, and mixtures thereof are especially preferred olefinic compounds. Of these compounds, isobutylene and diisobutylene are particularly desirable because of their availability and the particularly high sulfur containing compositions which can be prepared therefrom.

In another embodiment, the sulfurized organic compound is a sulfurized terpene compound. The term "terpene compound" as used in the specification and claims is intended to include the various isomeric terpene hydrocarbons having the empirical formula $C_{10}H_{16}$, such as contained in turpentine, pine oil and dipentenes, and the various synthetic and naturally occurring oxygen-containing derivatives. Mixtures of these various compounds generally win be utilized, especially when natural products such as pine oil and turpentine are used. Pine oil, for example, comprises a mixture of alpha-terpineol, beta-terpineol, alpha-fenchol, camphor, borneol/isoborneol, fenchone, estragole, dihydro alpha-terpineol, anethole, and other mono-terpene hydrocarbons. The specific ratios and amounts of the various components in a given pine oil will depend upon the particular source and the degree of purification. A group of pine oil-derived products are available commercially from Hercules Incorporated. It has been found that the pine oil products generally known as terpene alcohols available from Hercules Incorporated are particularly useful in the preparation of the sulfurized products of the invention. Pine oil products are available from Hercules under such designations as alpha-Terpineol, Terpineol 318 Prime, Yarmor 302, Herco pine oil, Yarmor 302W, Yarmor F and Yarmor 60.

In another embodiment, the sulfurized organic composition is at least one sulfur-containing material which comprises the reaction product of a sulfur source and at least one Diels-Alder adduct. Generally, the molar ratio of sulfur source to Diels-Alder adduct is in a range of from about 0.75 to about 4.0, preferably about 1 to about 2.0, more preferably about 1 to about 1.8. In one embodiment the molar ratio of sulfur to adduct is from about 0.8:1 to 1.2:1.

The Diels-Alder adducts are a well-known, art-recognized class of compounds prepared by the diene synthesis or Diels-Alder reaction. A summary of the prior art relating to this class of compounds is found in the Russian monograph, *Dienovyi Sintes,* Izdatelstwo Akademii Nauk SSSR, 1963 by A. S. Onischenko. (Translated into the English language by L. Mandel as A. S. Onischenko, *Diene Synthesis,* N.Y., Daniel Davey and Co., Inc., 1964.) This monograph and references cited therein are incorporated by reference into the present specification.

Basically, the diene synthesis (Diels-Alder reaction) involves the reaction of at least one conjugated diene with at least one ethylenically or acetylenically unsaturated compound, these latter compounds being known as dienophiles. Piperylene, isoprene, methylisoprene, chloroprene, and 1,3-butadiene are among the preferred dienes for use in preparing the Diels-Alder adducts. Examples of cyclic dienes are the cyclopentadienes, fulvenes, 1,3-cyclohexadienes, 1,3-cycloheptadienes, 1,3,5- cycloeptatrienes, cyclooctatetraene, and 1,3,5-cyclononatrienes.

A preferred class of dienophiles are those having at least one electron-accepting group selected from groups such as formyl, cyano, nitro, carboxy, carbohydrocarbyloxy, etc. Usually the hydrocarbyl and substituted hydrocarbyl groups, if not present, will not contain more than 10 carbon atoms each.

One preferred class of dienophiles are those wherein at least one carboxylic ester group represented by —C(O)O—$R_o$ where $R_o$ is the residue of a saturated aliphatic alcohol of up to about 40 carbon atoms, the aliphatic alcohol from which —$R_o$ is derived can be any of the above-described mono or polyhydric alcohols. Preferably the alcohol is a lower aliphatic alcohol, more preferably methanol, ethanol, propanol, or butanol.

In addition to the ethylenically unsaturated dienophiles, there are many useful acetylenically unsaturated dienophiles such as propiolaldehyde, methyl-ethynyl-ketone, propylethynylketone, propenylethynylketone, propiolic acid, propiolic nitrile, ethyl-propiolate, tetrolic acid, propargylaldehyde, acetylene-dicarboxylic acid, the dimethyl ester of acetylenedicarboxylic acid, dibenzoylacetylene, and the like.

Normally, the adducts involve the reaction of equimolar amounts of diene and dienophile. However, if the dienophile has more than one ethylenic linkage, it is possible for additional diene to react if present in the reaction mixture.

It is frequently advantageous to incorporate materials useful as sulfurization promoters in the reaction mixture. These materials may be acidic, basic or neutral. Useful neutral and acidic materials include acidified clays such as "Super Filtrol" (sulfuric acid treated diatomaceous earth), p-toluenesulfonic acid, phosphorus-containing reagents such as phosphorus acids (e.g., dialkyl-phosphorodithioic acids, phosphorus acid esters (e.g., triphenyl phosphate), phosphorus sulfides such as phosphorus pentasulfide and surface active agents such as lecithin.

The preferred promoters are basic materials. These may be inorganic oxides and salts such as sodium hydroxide, calcium oxide and sodium sulfide. The most desirable basic promoters, however, are nitrogen bases including ammonia and amines.

The amount of promoter material used is generally about 0.0005–2.0% of the combined weight of the terpene and olefinic compounds. In the case of the preferred ammonia and amine catalysts, about 0.0005–0.5 mole per mole of the combined weight is preferred, and about 0.001–0.1 is especially desirable.

Water is also present in the reaction mixture either as a promoter or as a diluent for one or more of the promoters recited hereinabove. The amount of water, when present, is usually about 1–25% by weight of the olefinic compound. The presence of water is, however, not essential and when certain types of reaction equipment are used it may be advantageous to conduct the reaction under substantially anhydrous conditions.

When promoters are incorporated into the reaction mixture as described hereinabove, it is generally observed that the reaction can be conducted at lower temperatures, and the product generally is lighter in color.

The sulfur source or reagent used for preparing any of the sulfur-containing materials of this invention may be, for example, sulfur, a sulfur halide such as sulfur monochloride or sulfur dichloride, a mixture of hydrogen sulfide and sulfur or sulfur dioxide, or the like. Sulfur, or mixtures of sulfur and hydrogen sulfide often are preferred. However, it will be understood that other sulfurization reagents may, when appropriate, be substituted therefor. Commercial sources of all the sulfurizing reagents are normally used for the purpose of this invention, and impurities normally associated with these commercial products may be present without adverse results.

When the sulfurization reaction is effected by the use of sulfur alone, the reaction is effected by merely heating the reagents with the sulfur at temperatures of from about 50° to 250° C., usually, from about 150° to about 210° C. The weight ratio of the materials to be sulfurized to sulfur is between about 5:1 and about 15:1, generally between about 5:1 and about 10:1. The sulfurization reaction is conducted with efficient agitation and generally in an inert atmosphere (e.g., nitrogen). If any of the components or reagents are appreciably volatile at the reaction temperature, the reaction vessel may be sealed and maintained under pressure. It is frequently advantageous to add the sulfur portionwise to the mixture of the other components.

When mixtures of sulfur and hydrogen sulfide are utilized in the process of the invention, the amounts of sulfur and hydrogen sulfide per mole of component(s) to be sulfurized are, respectively, usually about 0.3 to about 3 gram-atoms and about 0.1 to about 1.5 moles. A preferred range is from about 0.5 to about 2.0 gram-atoms and about 0.4 to about 1.25 moles, respectively, and the most desirable ranges are about 0.8 to about 1.8 gram-atoms, and about 0.4 to about 0.8 mole, respectively. In reaction mixture operations, the components are introduced at levels to provide these ranges. In semi-continuous operations, they may be admixed at any ratio, but on a mass balance basis, they are present so as to be consumed in amounts within these ratios. Thus, for example, if the reaction vessel is initially charged with sulfur alone, the terpene and/or olefinic compound and hydrogen sulfide are added incrementally at a rate such that the desired ratio is obtained.

When mixtures of sulfur and hydrogen sulfide are utilized in the sulfurization reaction, the temperature range of the sulfurization reaction is generally from about 50° C. to about 350° C. The preferred range is about 100° C. to about 200° C. with about 120° C. to about 180° C. being especially suitable. The reaction often is conducted under super atmospheric pressure which may be and usually is autogenous pressure (i.e., pressure which naturally developed during the course of the reaction), but may also be externally applied pressure. The exact pressure developed during the reaction is dependent upon such factors as design and operation of the system, the reaction temperature, and the vapor pressure of the reactants and products, and it may vary during the course of the reaction.

While it is preferred generally that the reaction mixture consists entirely of the components and reagents described above, the reaction also may be effected in the presence of an inert solvent (e.g., an alcohol, ether, ester, aliphatic hydrocarbon, halogenated aromatic hydrocarbon, etc.) which is liquid within the temperature range employed. When the reaction temperature is relatively high, for example, at about 200° C., there may be some evolution of sulfur from the product which is avoided is a lower reaction temperature such as from about 150°–170° C. is used.

In some instances, it may be desirable to treat the sulfurized product obtained in accordance with the procedures described herein to reduce active sulfur. The term "active sulfur" includes sulfur in a form which can cause staining of copper and similar materials, and standard tests are available to determine sulfur activity. As an alternative to the treatment to reduce active sulfur, metal deactivators can be used with the lubricants containing sulfurized compositions.

The following examples relate to sulfurized compositions useful as antioxidants in the present invention.

EXAMPLE AO-1

A reaction vessel is charged with 780 parts isopropyl alcohol, 752 parts water, 35 parts of a 50% by weight aqueous solution of sodium hydroxide, 60 parts of sulfuric acid treated diatomaceous earth (Super Filtrol available from Engelhard Corporation, Menlo Park, N.J.) and 239 parts of sodium sulfide. The mixture is stirred and heated to 77°–80° C. The reaction temperature is maintained for two hours. The mixture is cooled to 71° C. where 1000 parts of the sulfurized olefin prepared by reacting 337 parts of sulfur monochloride with 1000 parts of a mixture of 733 parts of 1-dodecene and 1000 parts of Neodene 1618, a $C_{16-18}$ olefin mixture available from Shell Chemical, is added to the mixture. The reaction mixture is heated to 77°–80° C. and the temperature is maintained until the chlorine content is a maximum of 0.5. The reaction mixture is vacuum stripped to 80° C. and 20 millimeters of mercury. The residue is filtered through diatomaceous earth. The filtrate has 19.0% sulfur and a specific gravity of 0.95.

EXAMPLE AO-2

A mixture of 100 parts of soybean oil and 50 parts of commercial $C_{16}$ α-olefins is heated to 175° C. under nitrogen and 17.4 parts of sulfur is added gradually, whereupon an exothermic reaction causes the temperature to rise to 205° C. The mixture is heated at 188°–200° C. for 5 hours, allowed to cool gradually to 90° C. and filtered to yield the desired product containing 10.13% sulfur.

EXAMPLE AO-3

A mixture of 100 parts of soybean oil, 3.7 parts of tall oil acid and 46.3 parts of commercial $C_{15-18}$ α-olefins is heated to 165° C. under nitrogen and 17.4 parts of sulfur is added. The temperature of the mixture rises to 191° C. It is maintained at 165°–200° C. for 7 hours and is then cooled to 90° C. and filtered. The product contains 10.13% sulfur.

EXAMPLE AO-4

A mixture of 93 parts (0.5 equivalent) of pine oil and 48 parts (1.5 equivalents) of sulfur is charged to a reaction vessel equipped with condenser, thermometer and stirrer. The mixture is heated to about 140° C. with nitrogen blowing and maintained at this temperature for about 28 hours. After cooling, 111 parts of a $C_{16}$ alpha-olefin (available from Gulf Oil Chemicals Company under the general trade name Gulftene 16) are added through an addition funnel, and after addition is complete, the addition funnel is replaced with a nitrogen tube. The reaction mixture is heated to 170° C. with nitrogen blowing and maintained at the temperature for about 5 hours. The mixture is cooled and filtered through a filter aid. The filtrate is the desired product having a sulfur content of 19.01% (theory 19.04%).

EXAMPLE AO-5

(a) A mixture comprising 400 grams of toluene and 66.7 grams of $AlCl_3$ is charged to a two-liter flask fitted with a stirrer, nitrogen inlet tube, and a solid carbon dioxide-cooled reflux condenser. A second mixture comprising 640 grams (5 moles) of butylacrylate and 240.8 grams of toluene is added to the $AlCl_3$ slurry over a 0.25-hour period while maintain the temperature within the range of 37°–58° C. Thereafter, 313 grams (5.8 moles) of butadiene are added to the slurry over a 2.75-hour period while maintaining the temperature of the reaction mass at 60°–61° C. by means of external cooling. The reaction mass is blown with nitrogen for about 0.33-hour and then transferred to a four-liter separatory funnel and washed with a solution of 150 grams of concentrated hydrochloric acid in 1100 grams of water. Thereafter, the product is subjected to two additional water washings using 1000 ml of water for each wash. The washed reaction product is subsequently distilled to remove unreacted butylacrylate and toluene. The residue of this first distillation step is subjected to further distillation at a pressure of 9–10 millimeters of mercury whereupon 785 grams of the desired adduct are collected over the temperature of 105°–115° C.

(b) The butadiene-butylacrylate Diels-Alder adduct prepared in (a) (4550 grams, 25 moles) and 1600 grams (50 moles) of sulfur flowers are charged to a 12 liter flask, fitted with stirrer, reflux condenser, and nitrogen inlet tube. The reaction mixture is heated at a temperature within the range of 150°–155° C. for 7 hours while passing nitrogen therethrough at a rate of about 0.5 standard cubic foot per hour (SCFH). After heating, the mass is permitted to cool to room temperature and filtered, the sulfur-containing product being the filtrate.

The antioxidant may also be an alkylated aromatic amine. Alkylated aromatic amines include compounds represented by the formula

(III)

wherein $Ar^1$ and $Ar^2$ are independently mononuclear or polynuclear, substituted or unsubstituted aromatic groups; and R is hydrogen, halogen, OH, $NH_2$, SH, $NO_2$ or a hydrocarbyl group of from 1 to about 50 carbon atoms. $Ar^1$ and $Ar^2$ may be any of the above-described aromatic groups. When Ar' and/or $Ar^2$ are substituted aromatic groups, the number of substituents on $Ar^1$ and/or $Ar^2$ range independently up to the number of positions available on $Ar^1$ and/or $Ar^2$ for substitution. These substituents are independently selected from the group consisting of halogen (e.g., chlorine, bromine, etc.), OH, $NH_2$, SH, $NO_2$ or hydrocarbyl groups of from 1 to about 50 carbon atoms.

In a preferred embodiment, the aromatic amine is represented by the formula

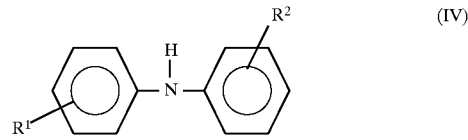

(IV)

wherein $R^1$ and $R^2$ are independently hydrogen or hydrocarbyl groups of from 1 to about 50 carbon atoms, preferably hydrocarbyl groups of from about 4 to about 20 carbon atoms. Examples of aromatic amines include p,p'-dioctyldiphenylamine; octylphenyl-beta-naphthylamine; octylphenyl-alpha-naphthylamine, phenyl-alphanaphthylamine; phenyl-beta-naphthylamine; p-octylphenyl-alpha-naphthylamine and 4-octylphenyl-1-octyl-beta-naphthylamine and di(nonylphenyl)amine, with di(nonylphenyl)amine preferred.

U.S. Pat. Nos. 2,558,285; 3,601,632; 3,368,975; and 3,505,225 disclose diarylamines useful in this invention. These patents are incorporated herein by reference.

The antioxidants used in the present invention may contain one or more of several types of phenolic compounds which may be metal-free phenolic compounds.

In one embodiment, the antioxidant of the present invention includes at least one metal-free hindered phenol. Alkylene coupled derivatives of said hindered phenols also can be used. Hindered phenols are defined (in the specification and claims) as those containing a sterically hindered hydroxyl group, and these include those derivatives of dihydroxy aryl compounds wherein the hydroxyl groups are in the o- or p-position to each other.

The metal-free hindered phenols may be represented by the following Formulae V–VII.

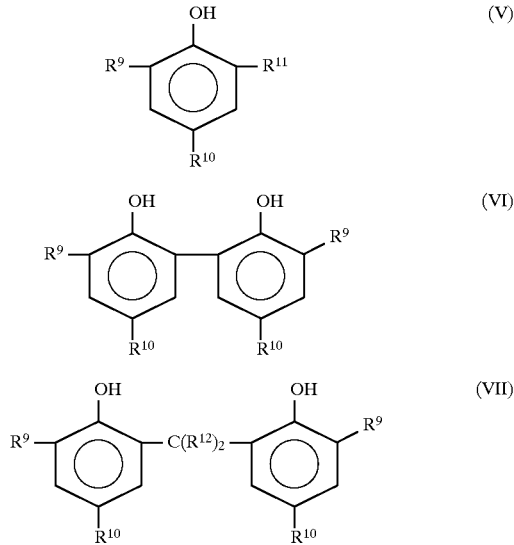

wherein each $R^9$ is independently an alkyl group containing from 1 to about 9 carbon atoms, each $R^{10}$ is hydrogen or an alkyl or alkoxy group, $R^{11}$ is hydrogen or an alkyl group containing from 1 to about 9 carbon atoms, and each $R^{12}$ is independently hydrogen or a methyl group. In one preferred embodiment, the phenol is characterized by Formula V wherein $R^{10}$ is hydrogen and $R^9$ and $R^{11}$ are alkyl groups containing from 1 to about 6 carbon atoms. In another embodiment, $R^{10}$ is an alkyl group containing from about 3 to about 50 carbon atoms, preferably about 6 to about 20, more preferably from about 6 to about 12. Examples of such groups include hexyl, heptyl, octyl, decyl, dodecyl, tripropenyl, tetrapropenyl, etc. Examples of $R^9$, $R^{10}$ and $R^{11}$ groups include propyl, isopropyl, butyl, secondary butyl, tertiary butyl, heptyl, octyl, and nonyl. Preferably, each $R^9$ and $R^{11}$ are tertiary groups such as tertiary butyl, tertiary amyl, etc.

The phenolic compounds of the type represented by Formula V may be prepared by various techniques, and in one embodiment, such phenols are prepared in stepwise manner by first preparing the para-substituted alkylphenol, and thereafter alkylating the para-substituted phenol in the 2- and/or 6position as desired. When it is desired to prepare coupled phenols of the type represented by Formulae VI and VII, the second step alkylation is conducted under conditions which result in the alkylation of only one of the positions ortho to the hydroxyl group. Examples of useful phenolic materials of the type represented by Formula V include: 2-t-butyl-4-heptylphenol; 2-t-butyl-4octylphenol; 2-t-butyl-4-dodecylphenol; 2,6-di-t-butyl-4-butylphenol; 2,6-di-t-butyl-4-heptylphenol; 2,6di-t-butyl-4-dodecylphenol; 2-methyl-6t-butyl-4-heptylphenol; 2,4-dimethyl-6t-butylphenol; 2,6t-butyl-4-ethylphenol; 4-t-butylcatechol; 2,4-di-t-butyl-p-cresol; 2,6di-t-butyl-4-methylphenol; and 2-methyl-6di-t-butyl-4-odecylphenol. These types of hindered phenols are available commercially from a variety of sources as pure compounds or mixtures. For example, Isonox® 103 is 99% min. 2,6di-t-butylphenol, and Isonox® 133 is 75% min 2,6-di-t-butylphenol. The Isonox® products are available from Schnectady International Chemical Division, Schnectady, N.Y.

Examples of the ortho coupled phenols of the type represented by Formula VI include: 2,2'-bis(6t-butyl-4-heptylphenol); 2,2'-bis(6t-butyl-4-octylphenol); 2,6bis-(1'-methylcyclohexyl)-4-methylphenol; and 2,2'-bis(6-t-butyl-4-dodecylphenol).

Alkylene-coupled phenolic compounds of the type represented by Formula VII can be prepared from the phenols represented by Formula V wherein $R^{11}$ is hydrogen by reaction of the phenolic compound with an aldehyde such as formaldehyde, acetaldehyde, etc. or a ketone such as acetone. Procedures for coupling of phenolic compounds with aldehydes and ketones are well known in the art, and the procedures do not need to be described in detail herein. To illustrate the process, the phenolic compound of the type represented by Formula V wherein $R^{11}$ is hydrogen is heated with a base in a diluent such as toluene or xylene, and this mixture is then contacted with the aldehyde or ketone while heating the mixture to reflux and removing water as the reaction progresses. Examples of phenolic compounds of the type represented by Formula VII include 2,2'-methylene-bis (6-t-butyl-4-heptylphenol); 2,2'-methylene-bis(6-t-butyl-4octylphenol); 2,2'-methylene-bis-(4-dodecyl-6-t-butylphenol); 2,2'-methylenebis-(4-octyl-6-t-butylphenol); 2,2'-methylene-bis-(4-octylphenol); 2,2'-methylene-bis-(4-dodecylphenol); 2,2'-methylene-bis-(4-heptylphenol); 2,2'-methylenebis(6-t-butyl-4-dodecylphenol); 2,2'-methylene-bis(6-t-butyl-4-tetrapropenylphenol); and 2,2'-methylene-bis(6-t-butyl-4-butylphenol).

The alkylene-coupled phenols may be obtained by reacting a phenol (2 equivalents) with 1 equivalent of an aldehyde or ketone. Lower molecular weight aldehydes are preferred and particularly preferred examples of useful aldehydes include formaldehyde, a reversible polymer thereof such as paraformaldehyde, trioxane, acetaldehyde, etc. As used in this specification and claims, the word "formaldehyde" shall be deemed to include such reversible polymers. The alkylene-coupled phenols can be derived from phenol or substituted alkylphenols, and substituted alkylphenols are preferred. The phenol must have an ortho or para position available for reaction with the aldehyde.

In one embodiment, the phenol will contain one or more alkyl groups which may or may not result in a sterically hindered hydroxyl group. Examples of hindered phenols which can be used in the formation of the alkylene-coupled phenols include: 2,4-dimethylphenol; 2,4-di-t-butylphenol; 2,6-di-t-butylphenol; 4-octyl-6-t-butylphenol; etc.

In one preferred embodiment, the phenol from which the alkylene-coupled phenols are prepared are phenols substituted in the para position with aliphatic groups containing at least 6 carbon atoms as described above. Generally, the alkyl groups contain from 6 to 12 carbon atoms. Preferred alkyl groups are derived from polymers of ethylene, propylene, 1-butene and isobutene, preferably propylene tetramer or trimer.

The reaction between the phenol and the aldehyde, polymer thereof or ketone is usually carried out between room temperature and about 150° C., preferably about 50°–125° C. The reaction preferably is carried out in the presence of an acidic or basic material such as hydrochloric acid, acetic acid, ammonium hydroxide, sodium hydroxide or potassium hydroxide. The relative amounts of the reagents used are not critical, but it is generally convenient to use about 0.3 to about 2.0 moles of phenol per equivalent of formaldehyde or other aldehyde.

The following examples illustrate the preparation of phenolic compounds of the type represented by Formulae V and VII.

EXAMPLE AO-6

A reaction vessel is charged with 3192 parts (12 moles) of a 4-tetrapropenylphenol. The phenol is heated to 80° C. in 30 minutes and 21 parts (0.2 mole) of a 93% sulfuric acid solution is added to the vessel. The mixture is heated to 85° C. and 1344 parts (24 moles) of isobutylene is added over 6 hours. The temperature is maintained between 85°–91° C. After introduction of isobutylene, the reaction is blown with nitrogen at 2 standard cubic feet per hour for 30 minutes at 85° C. Calcium hydroxide (6 parts, 0.08 mole) along with 12 parts of water is added to the reaction vessel. The mixture is heated to 130° C. under nitrogen for 1.5 hours. The reaction is vacuum stripped at 130° C. and 20 millimeters of mercury for 30 minutes. The residue is cooled to 90° C. and the residue is filtered through diatomaceous earth to give the desired product. The desired product has a specific gravity of 0.901 and a percent hydroxyl (Grignard) equals 4.25 (theoretical 4.49).

EXAMPLE AO-7

A reaction vessel is charged with 798 parts (3 moles) of 4-tetrapropenylphenol. The phenol is heated to 95°–100° C. where 5 parts of a 93% solution of sulfuric acid is added to the vessel. 168 parts (3 moles) of isobutylene is added to the vessel over 1.7 hours at 100° C. After introduction of the isobutylene the reaction is blown with nitrogen at 2 standard cubic feet per hour for one-half hour at 100° C. 890 parts of the above-described phenol (2.98 moles) is added to a reaction vessel and heated to 34°–40° C. A 37% aqueous formaldehyde solution (137 grams, 1.7 moles) is added to the vessel. The mixture is heated to 135° C. with removal of water. Nitrogen blowing at 1.5 SCFH begins at 105°–110° C. The reaction is held at 120° C. for 3 hours under nitrogen. The reaction is cooled to 83° C. where 4 parts (0.05 mole) of a 50% aqueous sodium hydroxide solution is added to the vessel. The reaction is heated to 135° C. under nitrogen. The reaction is vacuum stripped to 135° C. and 20 millimeters of mercury for 10 minutes. The reaction is cooled to 95° C. and the residue is filtered through diatomaceous earth. The product has a percent hydroxyl (Grignard) of 5.47 (theoretical 5.5) and a molecular weight (vapor phase osmometry) of 682 (theoretical 667).

EXAMPLE AO-8

The general procedure of Example AO-6 is repeated except that the 4-tetrapropenylphenol is replaced by an equivalent amount of tri-propylene phenol. The substituted phenol obtained in this manner contains 5.94% hydroxyl.

In another embodiment, the antioxidants used in the present invention may be metal-free (or ashless) alkylphenol sulfides. The alkylphenols from which the sulfides are prepared also may comprise phenols of the type discussed above and represented by Formula V wherein $R^{11}$ is hydrogen. For example, the alkylphenols which can be converted to alkylphenol sulfides include: 2-t-butyl-4-heptylphenol; 2-t-butyl-4-octylphenol; and 2-t-butyl-4-dodecylphenol.

The term "alkylphenol sulfides" is meant to include di-(alkylphenol)-monosulfides, disulfides, polysulfides, and other products obtained by the reaction of the alkylphenol with sulfur monochloride, sulfur dichloride or elemental sulfur. One mole of phenol is reacted with about 0.5–1.5 moles, or higher, or sulfur compound. For example, the alkylphenol sulfides are readily obtained by mixing, one mole of an alkylphenol and 0.5–2.0 moles of sulfur dichloride. The reaction mixture is usually maintained at about 100° C. for about 2–5 hours, after which time the resulting sulfide is dried and filtered. When elemental sulfur is used, temperatures of about 150°–250° C. or higher are typically used. It is also desirable that the drying operation be conducted under nitrogen or a similar inert gas.

Suitable basic alkylphenol sulfides are disclosed, for example, in U.S. Pat. Nos. 3,372,116; 3,410,798; and 4,021,419, which are hereby incorporated by reference.

The sulfur-containing phenolic compositions described in U.S. Pat. No. 4,021,419 are obtained by sulfurizing a substituted phenol with sulfur or a sulfur halide and thereafter reacting the sulfurized phenol with formaldehyde or a reversible polymer thereof. Alternatively the substituted phenol can be first reacted with formaldehyde and thereafter reacted with sulfur or a sulfur halide to produce the desired alkylphenol sulfide. The disclosure of U.S. Pat. No. 4,021,419 is hereby incorporated by reference for its disclosure of such compounds, and methods for preparing such compounds. A synthetic oil of the type described below is used in place of any mineral or natural oils used in the preparation of the salts for use in this invention.

In another embodiment, the antioxidant may be phenothiazine, substituted phenothiazines, or derivatives such as represented by Formula VIII

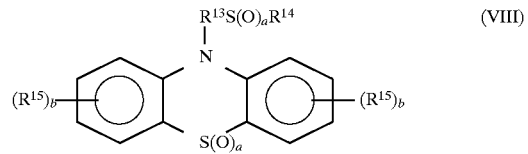

wherein $R^{14}$ is selected from the group consisting of higher alkyl groups, or an alkenyl, aryl, alkaryl or aralkyl group and mixtures thereof; $R^{13}$ is an alkylene, alkenylene or an aralkylene group, or mixtures thereof; each $R^{15}$ is independently alkyl, alkenyl, aryl, alkaryl, arylalkyl, halogen, hydroxyl, alkoxy, alkylthio, arylthio, or fused aromatic rings, or mixtures thereof; each a is independently 0, 1 or 2, and each b is independently 0 or greater.

In another embodiment, the phenothiazine derivatives may be represented by Formula IX

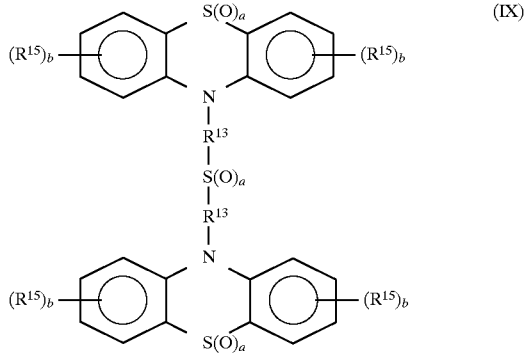

wherein $R^{13}$, $R^{14}$, $R^{15}$, a and b are as defined with respect to Formula VIII.

The above-described phenothiazine derivatives, and methods for their preparation are described in U.S. Pat. No. 4,785,095, and the disclosure of this patent is hereby incorporated by reference for its teachings of such methods and compounds. In one embodiment, a dialkyldiphenylamine is treated with sulfur at an elevated temperature such as in the range of 145° C. to 205° C. for a sufficient time to complete the reaction. A catalyst such as iodine may be utilized to establish the sulfur bridge.

Phenothiazine and its various derivatives can be converted to compounds of Formula VIII by contacting the phenothiazine compound containing the free NH group with a thio alcohol of the formula $R^{14}SR^{13}OH$ where $R^{14}$ and $R^{13}$ are defined with respect to Formula VIII. The thio alcohol may be obtained by the reaction of a mercaptan $R^{14}SH$ with an alklene oxide under basic conditions. Alternatively, the thio alcohol may be obtained by reacting a terminal olefin with mercaptoethanol under free radical conditions. The reaction between the thio alcohol and the phenothiazine compound generally is conducted in the presence of an inert solvent such as toluene, benzene, etc. A strong acid catalyst such as sulfuric acid or para-toluene sulfonic acid at about 1 part to about 50 parts of catalyst per 1000 parts of phenothiazine is preferred. The reaction is conducted generally at reflux temperature with removal of water as it is formed. Conveniently, the reaction temperature may be maintained between 80° C. and 170° C.

When it is desired to prepare compounds of the type represented by Formulae VIII and IX wherein a is 1 or 2, i.e., sulfones or sulfoxides, the derivatives prepared by the reaction with the thio alcohols described above are oxidized with an oxidizing agent such as hydrogen peroxide in a solvent such as glacial acetic acid or ethanol under an inert gas blanket. The partial oxidation takes place conveniently at from about 20° C. to about 150° C. The following examples illustrate the preparation of phenothiazines which may be utilized as a non-phenolic antioxidant in the compositions of the present invention.

EXAMPLE AO-9

One mole of phenothiazine is placed in a one-liter, round bottom flask with 300 ml. of toluene. A nitrogen blanket is maintained in the reactor. To the mixture of phenothiazine and toluene is added 0.05 mole of sulfuric acid catalyst. The mixture is then heated to reflux temperature and 1.1 moles of n-dodecylthio-ethanol is added dropwise over a period of approximately 90 minutes. Water is continuously removed as it is formed in the reaction process.

The reaction mixture is continuously stirred under reflux until substantially no further water is evolved. The reaction mixture is then allowed to cool to 90° C. The sulfuric acid catalyst is neutralized with sodium hydroxide. The solvent is then removed under a vacuum of 2 kPa at 110° C. The residue is filtered giving a 95% yield of the desired product.

In another embodiment, the antioxidant is a transition metal-containing composition. The transition metal-containing antioxidant is oil-soluble. The compositions generally contain at least one transition metal selected from titanium, manganese, cobalt, nickel, copper, and zinc, preferably manganese, copper, and zinc, more preferably copper. The metals may be in the form of nitrates, nitrites, halides, oxyhalides, carboxylates, borates, phosphates, phosphites, sulfates, sulfites, carbonates and oxides. The transition metal-containing composition is generally in the form of a metal-organic compound complex. The organic compounds include carboxylic acids and esters, mono- and dithiophosphoric acids, dithiocarbamic acids and dispersants. Generally, the transition metal-containing compositions contain at least about 5 carbon atoms to render the compositions oil-soluble.

In one embodiment, the organic compound is a carboxylic acid. The carboxylic acid may be a mono- or polycarboxylic acid containing from 1 to about 10 carboxylic groups and 2 to about 75 carbon atoms, preferably 2 to about 30, more preferably 2 to about 24. Examples of monocarboxylic acids include 2-ethylhexanoic acid, octanoic acid, decanoic acid, oleic acid, linoleic acid, stearic acid and gluconic acid. Examples of polycarboxylic acids include succinic, malonic, citraconic acids as well as substituted versions of these acids. The carboxylic acid may be one of the above-described hydrocarbyl-substituted carboxylic acylating agents.

In another embodiment, the organic compound is a mono- or dithiocarbamic acid. Mono- or dithiocarbamic acid is prepared by reacting carbon disulfide or carbon oxysulfide with a primary or secondary amine. The amines may be any of the amines described above.

In another embodiment, the organic compound may be any of the phenols or aromatic amines described above or any of the dispersants described in more detail below in the discussion of performance additives. In a preferred embodiment, the transition metal-containing composition is a lower carboxylic acid-transition metal-dispersant complex. The lower alkyl carboxylic acids contain from 1 to about 7 carbon atoms and include formic acid, acetic, propionic, butanoic, 2-ethylhexanoic, benzoic acid, and salicylic acid. The dispersant may be any of the dispersants described above, preferably the dispersant is a nitrogen-containing carboxylic dispersant. The transition metal complex is prepared by blending a lower carboxylic acid salt of a transition metal with a dispersant at a temperature from about 25° C. up to the decomposition temperature of the reaction mixture, usually from about 25° C. up to about 100° C. A solvent such a xylene, toluene, naphtha or mineral oil may be used.

EXAMPLE AO-10

The metal complex is obtained by heating at 160° C. for 32 hours 50 parts of copper diacetate monohydrate, 283 parts of 100 neutral mineral oil, 250 milliliters of xylene and 507 parts of an acylated nitrogen intermediate prepared by reacting 4,392 parts of a polybutene-substituted succinic anhydride (prepared by the reaction of a chlorinated polybutene having a number average molecular weight of 1000 and a chlorine content of 4.3% and 20% molar excess of maleic anhydride) with 540 parts of an alkylene amine polyamine mixture of 3 parts by weight of triethylene tetramine and 1 part by weight of diethylene triamine, and 3240 parts of 100 neutral mineral oil at 130° C.–240° C. for 3.5 hours. The reaction is vacuum stripped to 110° C. and 5 millimeters of mercury. The reaction is filtered through diatomaceous earth to yield a filtrate which has 59% by weight oil, 0.3% by weight copper and 1.2% by weight nitrogen.

In one embodiment, the antioxidant is a phosphorus acid ester prepared by reacting phosphorus acid or anhydride with an alcohol containing from one to about 30, or from about 3 to about 12 carbon atoms. The phosphorus acid or anhydride is generally an inorganic phosphorus reagent, such as phosphorus pentoxide, or a phosphorus sulfide, including phosphorus pentasulfide. Examples of useful phosphorus acid esters include the phosphoric acid esters prepared by reacting a phosphoric acid or anhydride with cresol. An example of these phosphorus acid esters is tricresylphosphate.

In another embodiment, the antioxidant is a thiophosphorus acid ester or salt thereof. The thiophosphorus acid esters may be prepared by reacting phosphorus sulfides with alcohols, such as those described above.

In another embodiment, the antioxidant is a dihydrocarbyl dithiophosphoric acid or dihydrocarbyl phosphorodithioic acid. Generally, each hydrocarbyl group independently contains from about 3 to about 30, or from about 3 up to about 12 carbon atoms.

The dithiophosphoric acid may be reacted with an epoxide or a polyhydric alcohol, such as glycols. This reaction product may be used alone, or further reacted with a phosphorus acid, anhydride, or lower ester. The epoxide is generally an aliphatic epoxide or a styrene oxide. Examples of useful epoxides include ethylene oxide, propylene oxide, butene oxide, etc. The dithiophosphoric acids, glycols, epoxides, inorganic phosphorus reagents and methods of reacting the same are described in U.S. Pat. No. 3,197,405 and U.S. Pat. No. 3,544,465 which are incorporated herein by reference for their disclosure to these.

Useful phosphorus acid esters include those prepared by reacting phosphorus pentoxide with hydroxypropyl O,O-di(4-methyl-2-pentyl)phosphorodithioate (prepared by reacting di(4-methyl-2-pentyl)-phosphorodithioic acid with 1.3 moles of propylene oxide at 25° C.) or O,O-di(isopropyl) phosphorodithioate (prepared by reacting diisopropyl phosphorodithioic acid with propylene oxide at 50° C.).

Phosphorus acid esters may be reacted with an amine or metallic base to form an amine or metal salt. The amine salts of the phosphorus acid esters may be formed from ammonia, or an amine, including monoamines and polyamines. Useful amines include those amines disclosed in U.S. Pat. No. 4,234,435 at Col. 21, line 4 to Col. 27, line 50, these passages being incorporated herein by reference. Tertiary aliphatic primary amines are particularly useful. Useful amine salts reaction products of a commercial aliphatic primary amine, having an average molecular weight of 191 in which the aliphatic radical is a mixture of tertiary alkyl radicals containing from 11 to 14 carbon atom, with phosphorus acid esters selected from reacting phosphorus pentoxide with hydroxypropyl O,O-di(4-methyl-2-pentyl) phosphorodithioate (prepared by reacting di(4-methyl-2-pentyl)-phosphorodithioic acid with 1.3 moles of propylene oxide at 25° C.) or O,O-di(isopropyl)phosphorodithioate (prepared by reacting diisopropyl phosphorodithioic acid with propylene oxide at 50° C.).

The antioxidant useful in the compositions of the present invention may be at least one metal dihydrocarbyl dithiophosphate characterized by the formula

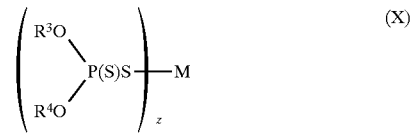

$$\left( \begin{array}{c} R^3O \\ \phantom{R}\diagdown \\ \phantom{RR}P(S)S \\ \phantom{R}\diagup \\ R^4O \end{array} \right)_z M \qquad (X)$$

wherein $R^3$ and $R^4$ are each independently hydrocarbyl groups containing from 2 to about 24 carbon atoms, preferably from 3 to about 12, M is a metal, and z is an integer equal to the valence of M.

The hydrocarbyl groups $R^3$ and $R^4$ in the dithiophosphate may be alkyl, cycloalkyl, aralkyl or alkaryl groups. Illustrative alkyl groups include isopropyl, isobutyl, n-butyl, sec-butyl, the various amyl groups, n-hexyl, methylisobutyl carbinyl, heptyl, 2-ethylhexyl, diisobutyl, isooctyl, nonyl, behenyl, decyl, dodecyl, tridecyl, etc. Illustrative lower alkylphenyl groups include butylphenyl, amylphenyl, heptylphenyl, etc. Cycloalkyl groups likewise are useful and these include chiefly cyclohexyl and the lower alkyl-cyclohexyl radicals. Many substituted hydrocarbon groups may also be used, e.g., chloropentyl, dichlorophenyl, and dichlorodecyl.

The phosphorodithioic acids from which the metal salts useful in this invention are prepared are well known. Examples of dihydrocarbyl phosphorodithioic acids and metal salts, and processes for preparing such acids and salts are found in, for example, U.S. Pat. Nos. 4,263,150; 4,289, 635; 4,308,154; and 4,417,990. These patents are hereby incorporated by reference for such disclosures.

The phosphorodithioic acids are prepared by the reaction of phosphorus pentasulfide with an alcohol or phenol or mixtures of alcohols. The reaction involves four moles of the alcohol or phenol per mole of phosphorus pentasulfide, and may be carried out within the temperature range from about 50° C. to about 200° C. Thus the preparation of O,O-di-n-hexyl phosphorodithioic acid involves the reaction of phosphorus pentasulfide with four moles of n-hexyl alcohol at about 100° C. for about two hours. Hydrogen sulfide is liberated and the residue is the defined acid. The preparation of the metal salt of this acid may be effected by reaction with metal oxide. Simply mixing and heating these two reactants is sufficient to cause the reaction to take place and the resulting product is sufficiently pure for the purposes of this invention.

The metal salts of dihydrocarbyl dithiophosphates which are useful in this invention include those salts containing Group I metals, Group II metals, aluminum, lead, tin, molybdenum, manganese, cobalt, and nickel. Group I and Group II (including Ia, Ib, IIa and IIb) are defined in the Periodic Table of the Elements in the Merck Index, 11th Edition (1989). The Group II metals, aluminum, tin, iron, cobalt, lead, molybdenum, manganese, nickel and copper are among the preferred metals. Zinc and copper are especially useful metals. In one embodiment, the lubricating compositions contain a zinc dihydrocarbyl dithiophosphate and a copper dihydrocarbyl dithiophosphate. Examples of metal compounds which may be reacted with the acid include lithium oxide, lithium hydroxide, sodium hydroxide, sodium carbonate, potassium hydroxide, potassium carbonate, silver oxide, magnesium oxide, magnesium hydroxide, calcium oxide, zinc hydroxide, strontium hydroxide, cadmium oxide, cadmium hydroxide, barium oxide, aluminum oxide, iron carbonate, copper hydroxide, copper oxide, lead hydroxide, tin butylate, cobalt hydroxide, nickel hydroxide, nickel carbonate, zinc oxide, etc.

In some instances, the incorporation of certain ingredients such as small amounts of the metal acetate or acetic acid in conjunction with the metal reactant will facilitate the reaction and result in an improved product. For example, the use of up to about 5% of zinc acetate in combination with the required amount of zinc oxide facilitates the formation of a zinc phosphorodithioate.

In one preferred embodiment, the alkyl groups $R^3$ and $R^4$ are derived from secondary alcohols such as isopropyl alcohol, secondary butyl alcohol, 2-pentanol, 2-methyl-4-pentanol, 2-hexanol, 3-hexanol, etc.

Especially useful metal phosphorodithioates can be prepared from phosphorodithioic acids which in turn are prepared by the reaction of phosphorus pentasulfide with mixtures of alcohols. In addition, the use of such mixtures enables the utilization of cheaper alcohols which in themselves may not yield oil-soluble phosphorodithioic acids or salts thereof. Thus a mixture of isopropyl and hexyl alcohols can be used to produce a very effective, oil-soluble metal phosphorodithioate. For the same reason mixtures of phosphorodithioic acids can be reacted with the metal compounds to form less expensive, oil-soluble salts.

The mixtures of alcohols may be mixtures of different primary alcohols, mixtures of different secondary alcohols or mixtures of primary and secondary alcohols. Examples of useful mixtures include: n-butanol and n-octanol; n-pentanol and 2-ethyl-1-hexanol; isobutanol and n-hexanol; isobutanol and isoamyl alcohol; isopropanol and 2-methyl-4-pentanol; isopropanol and sec-butyl alcohol; isopropanol and isooctyl alcohol; etc. Particularly useful alcohol mixtures are mixtures of secondary alcohols containing at least about 20 mole percent of isopropyl alcohol, and in a preferred embodiment, at least 40 mole percent of isopropyl alcohol.

Generally, the oil compositions of the present invention will contain varying amounts of one or more of the above-identified metal dithiophosphates such as from about 0.01 to about 2% by weight, and more generally from about 0.01 to about 1% by weight based on the weight of the total oil composition. The metal dithiophosphates are added to the lubricating oil compositions of the invention to improve the anti-wear and antioxidant properties of the oil compositions.

The following examples illustrate the preparation of metal phosphorodithioates.

EXAMPLE AO-11

A phosphorodithioic acid is prepared by reacting a mixture of alcohols comprising 6 moles of 4-methyl-2-pentanol and 4 moles of isopropyl alcohol with phosphorus pentasulfide. The phosphorodithioic acid then is reacted with an oil slurry of zinc oxide. The amount of zinc oxide in the slurry is about 1.08 times the theoretical amount required to completely neutralize the phosphorodithioic acid. The oil solution of the zinc phosphorodithioate obtained in this manner (10% oil) contains 9.5% phosphorus, 20.0% sulfur and 10.5% zinc.

Additional specific examples of metal phosphorodithioates useful in the lubricating oils of the present invention are listed in the following table. These metal dithiophosphates are prepared by the general procedure of Example AO-11.

TABLE

Metal Phosphorodithioates

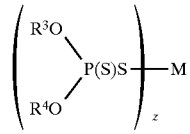

| Example | $R^3$ | $R^4$ | M | z |
|---|---|---|---|---|
| AO-12 | (isopropyl + isooctyl) (60:40)$_m$ | | Zn | 2 |
| AO-13 | n-nonyl | n-nonyl | Ba | 2 |
| AO-14 | cyclohexyl | cyclohexyl | Zn | 2 |
| AO-15 | isobutyl | isobutyl | Zn | 2 |
| AO-16 | hexyl | hexyl | Ca | 2 |
| AO-17 | n-decyl | n-decyl | Zn | 2 |
| AO-18 | 4-methyl-2-pentyl | 4-methyl-2-pentyl | Cu | 2 |
| AO-19 | (n-butyl + dodecyl) (1:1)w | | Zn | 2 |
| AO-20 | (isopropyl + isooctyl) (1:1)w | | Ba | 2 |
| AO-21 | (isopropyl + 4-methyl-2 pentyl) + (40:60)m | | Cu | 2 |
| AO-22 | (isobutyl + isoamyl) (65:35)m | | Zn | 2 |
| AO-23 | (isopropyl + sec-butyl) (40:60)m | | Zn | 2 |

Another class of the phosphorodithioate additives contemplated for use in the composition of this invention comprises the adducts of the metal phosphorodithioates described above with an epoxide. The metal phosphorodithioates useful in preparing such adducts are for the most part the zinc phosphorodithioates. The epoxides may be alkylene oxides or arylalkylene oxides. The arylalkylene oxides are exemplified by styrene oxide, p-ethylstyrene oxide, alpha-methylstyrene oxide, 3-beta-naphthyl-1,1,3-butylene oxide, m-dodecylstyrene oxide, and pchlorostyrene oxide. The alkylene oxides include principally the lower alkylene oxides in which the alkylene radical contains 8 or less carbon atoms. Examples of such lower allylene oxides are ethylene oxide, propylene oxide, 1,2-butene oxide, trimethylene oxide, tetramethylene oxide, butadiene monoepoxide, 1,2-hexene oxide, and epichlorohydrin. Other epoxides useful herein include, for example, butyl 9,10-epoxy-stearate, epoxidized soya bean oil, epoxidized tung oil, and epoxidized copolymer of styrene with butadiene.

The adduct may be obtained by simply mixing the metal phosphoro-dithioate and the epoxide. The reaction is usually exothermic and may be carried out within wide temperature limits from about 0° C. to about 300° C. Because the reaction is exothermic, it is best carried out by adding one reactant, usually the epoxide, in small increments to the other reactant in order to obtain convenient control of the temperature of the reaction. The reaction may be carried out in a solvent such as benzene, toluene, xylene, mineral oil, naphtha, or n-hexene.

The chemical structure of the adduct is not known. For the purpose of this invention adducts obtained by the reaction of one mole of the phosphorodithioate with from about 0.25 mole to 5 moles, usually up to about 0.75 mole or about 0.5 mole of a lower alkylene oxide, particularly ethylene oxide and propylene oxide, have been found to be especially useful and therefore are preferred.

The preparation of such an adduct is more specifically illustrated by the following example.

EXAMPLE AO-24

A reactor is charged with 2365 parts (3.33 moles) of a zinc isopropyl-isooctyl phosphorodithioate (wherein the molar ratio of isopropyl to isooctyl is (1:0.7), and while stirring at room temperature, 38.6 parts (0.67 mole) of propylene oxide are added with an exotherm of from 24°–31° C. The mixture is heated to and maintained at 80°–90° C. for 3 hours and then vacuum stripped to 101° C. at 7 mm.Hg. The residue is filtered using a filter aid, and the filtrate is an oil solution (11.8% oil) of the desired salt containing 17.1% sulfur, 8.17% zinc and 7.44% phosphorus.

Another class of the phosphorodithioate antioxidants contemplated as useful in the compositions of the invention comprises mixed metal salts of (a) at least one phosphorodithioic acid as defined above and (b) at least one aliphatic or alicyclic carboxylic acid. The carboxylic acid may be a monocarboxylic or polycarboxylic acid, usually containing from 1 to about 3 carboxy groups, preferably one. It may contain from about 2 to about 40, preferably from about 2 to about 20 carbon atoms, and advantageously about 5 to about 20 carbon atoms. The carboxylic acid may be any of the above-described carboxylic acids. The preferred carboxylic acids are those having the formula $R^5C(O)OH$, wherein $R^5$ is an aliphatic or alicyclic hydrocarbon-based radical preferably free from acetylenic unsaturation. Suitable acids include the butanoic, pentanoic, hexanoic, octanoic, nonanoic, decanoic, dodecanoic, octadecanoic and eicosanoic acids, as well as olefinic acids such as oleic, linoleic, and linolenic acids and linoleic acid dimer. For the most part, $R^5$ is a saturated aliphatic group and especially a branched alkyl group such as the isopropyl or 3-heptyl group. Illustrative polycarboxylic acids are succinic, alkyl- and alkenyl succinic, adipic, sebacic and citric acids.

The mixed metal salts may be prepared by merely blending a metal salt of a phosphorodithioic acid with a metal salt of a carboxylic acid in the desired ratio. The ratio of equivalents of phosphorodithioic to carboxylic acid salts is between about 0.5:1 to about 400:1. Preferably, the ratio is between about 0.5:1 and about 200:1. Advantageously, the ratio can be from about 0.5:1 to about 100:1, preferably from about 0.5:1 to about 50:1, and more preferably from about 0.5:1 to about 20:1. Further, the ratio can be from about 0.5:1 to about 4.5:1, preferably about 2.5:1 to about 4.25:1. For this purpose, the equivalent weight of a phosphorodithioic acid is its molecular weight divided by the number of -P(S)SH groups therein, and that of a carboxylic acid is its molecular weight divided by the number of carboxy groups therein.

A second and preferred method for preparing the mixed metal salts useful in this invention is to prepare a mixture of the acids in the desired ratio and to react the acid mixture with one of the above described metal compounds. When this method of preparation is used, it is frequently possible to prepare a salt containing an excess of metal with respect to the number of equivalents of acid present; thus, mixed metal salts containing as many as 2 equivalents and especially up to about 1.5 equivalents of metal per equivalent of acid may be prepared. The equivalent of a metal for this purpose is its atomic weight divided by its valence.

Variants of the above-described methods may also be used to prepare the mixed metal salts useful in this invention. For example, a metal salt of either acid may be blended with an acid of the other, and the resulting blend reacted with additional metal base.

The temperature at which the mixed metal salts are prepared is generally between about 30° C. and about 150° C., preferably up to about 125° C. If the mixed salts are prepared by neutralization of a mixture of acids with a metal base, it is preferred to employ temperatures above about 50° C. and especially above about 75° C. It is frequently advantageous to conduct the reaction in the presence of a substantially inert, normally liquid organic diluent such as naphtha, benzene, xylene, mineral oil or the like. If the diluent is mineral oil or is physically and chemically similar to mineral oil, it frequently need not be removed before using the mixed metal salt as an additive for lubricants or functional fluids.

U.S. Pat. Nos. 4,308,154 and 4,417,990 describe procedures for preparing these mixed metal salts and disclose a number of examples of such mixed salts. Such disclosures of these patents are hereby incorporated by reference.

The preparation of a mixed salt is illustrated by the following example.

EXAMPLE AO-25

A mixture of 67 parts (1.63 equivalents) of zinc oxide and 48 parts of mineral oil is stirred at room temperature and a mixture of 401 parts (1 equivalent) of di-(2-ethylhexyl) phosphorodithioic acid and 36 parts (0.25 equivalent) of 2-ethylhexanoic acid is added over 10 minutes. The temperature increases to 40° C. during the addition. When addition is complete, the temperature is increased to 80° C. for 3 hours. The mixture is then vacuum stripped at 100° C. to yield the desired mixed metal salt as a 91% solution in mineral oil.

Other antioxidants include metal thiocarbamates, such as zinc dioctyldithiocarbamate, or barium diheptylphenyl dithiocarbamate; dithiocarbamate esters, such as reaction products of an amine (e.g., butylamine), carbon disulfide, and one or more of the above unsaturated amide, ester, acid, or ether, such as acrylic, methacrylic, maleic, or fumaric acids, esters, or salts and acrylamides; and dithiocarbamates, such as alkylene coupled dithiocarbamates, which include methylene or phenylene coupled bis (butyldithiocarbamates), and bis-(s-alkyldithiocarbamoyl) disulfides, which are known and referred to as sulfur-coupled thiocarbamates.

The antioxidants useful in the compositions of the present invention may also be tocopherols. Tocopherols are a member of the family of chroman compounds, and various tocopherols are known and are described in the Merck Index, 11th Edition (1989). The tocopherols described therein include alpha tocopherol, beta tocopherol, delta tocopherol, gamma tocopherol, omega tocopherol, epsilon tocopherol, etc. It is also possible in the present invention to use synthetic tocopherol compounds. The synthetic tocopherol compounds are typically obtained by alkylating the ring structure to synthetically form a chroman compound. The primary difference between synthetic and natural tocopherols is that natural tocopherols have a substantial degree of optical rotation. The synthetic tocopherols due to their formation are optically balanced in both the dextro and levo forms. Thus, the synthetic tocopherols do not exhibit optical rotation. Mixtures of tocopherols may also be used as antioxidants in the compositions of the present invention.

Other Performance Additives.

The compositions of this invention, and particularly, the lubricating oils, functional fluids, greases and aqueous compositions of the invention may contain other performance additives such as detergents, dispersants, metal deactivators, antiwear agents, extreme-pressure agents, viscosity index modifiers, pour point depressants, foam inhibitors, demulsifiers, friction-modifiers, and corrosion-inhibitors. Some of the antioxidants described above also function as antiwear agents, extreme-pressure agents, or corrosion-inhibitors, but supplemental antiwear agents, extreme-pressure agents and corrosion-inhibitors often are desirable in the compositions of the invention.

The metal deactivators which may be included in the composition of the present invention generally are triaolecontig compounds and more particularly, benzotriazole and substituted benzotriazoles.

A wide variety of aromatic triazoles are known, many of which are described in detail in "Benztriole: A Novel Synthetic Auxiliary," Katritsky, Rachwal and Hitchings, *Tetrahedron*, Vol. 27, No. 16/17, pp. 2683–2732, 1991 (Pergamon Press plc), along with methods for their preparation.

It is preferred that the triazole be a substituted benzotriazole, in order that the solubility of the material in lubricating oil be sufficient to provide easy preparation, storage, and use of the composition. Thus it is preferred that the triazole contain a hydrocarbyl substituent. The location of the substitution is not critical. In one embodiment the substitution is on the benzene ring. In this case there may be 1 through 4 hydrocarbyl substituents, but most commonly there will be a single hydrocarbyl substituent. It is preferred that the hydrocarbyl substituent be an alkyl, aryl, or aralkyl substituent, and most commonly it will be an alkyl group. Alkyl groups include groups from methyl up to long chain alkyl groups such as alkyl oligomers or polymers, including ethyl, propyl, butyl, amyl, hexyl, and octyl groups, both normal and branched, as well as longer carbon chains such as $C_{12}$ to $C_{24}$, including $C_{18}$, which may be saturated or unsaturated. Examples of suitable aromatic triazoles are benzotriazole, alkyl-substituted benzotriazole (e.g., tolyltriazole, ethylbenzotriazole, hexylbenzotriazole, octylbenzotriazole, etc.), and alkylaryl- or arylalkyl-substituted benzotriazole and substituted benzotriazoles where the substituent may be hydroxy, alkoxy, halo (especially chloro), nitro, carboxy and carboxyalkoxy. Preferably, the triazole is a benzotriazole or an alkylbenzotriazole in which the alkyl group contains 1 to about 20 carbon atoms, preferably 1 to about 8 carbon atoms. Benzotriazole and tolyltriazole are particularly preferred.

In another embodiment there is substitution on at least one of the nitrogen atoms of the triazole group. One such type of substitution is the formation of a salt, preferably a salt of a benzotriazole anion and a quaternary ammonium cation. It is preferred, in order to impart additional hydrocarbon solubility to such a salt, that the quaternary ammonium cation be derived from an amine which contains at least one hydrocarbyl group as described above, preferably at least one alkyl group of at least 6 carbon atoms. Di-2-ethylhexylamine is a suitable amine for forming such a cation.

Alternatively, the substitution on one of the nitrogen atoms of the triazole can be accomplished by reacting a benzotriazole with an aldehyde and a primary or secondary amine or an alcohol. Numerous examples of such substituted triazoles are disclosed in the Katritzky reference mentioned above.

The aldehyde used in preparing this embodiment can be alkyl, aryl, alkylaryl, or arylalkyl containing 1 to about 12 or more carbon atoms. Included are benzaldehyde, salicylaldehyde, and 2-ethylhexanal. If it is desired that the aldehyde moiety itself be used to impart hydrocarbon solubility to the triazole, then the aldehyde should be selected to have a suitable large number of carbon atoms, such as at last 4 or preferably at least about 6. However, it is also possible that the primary or secondary amine or alcohol reactant will impart a large portion of the hydrocarbon solubility to the molecule. In that case lower molecular weight aldehydes can be conveniently used. Formaldehyde and paraformaldehyde are preferred.

The amine used in the preparation of this type of triazole derivative can be one or more mono- or polyamines. These monoamines and polyamines can be primary amines or preferably secondary amines. (It is believed that tertiary amines may also be used if the desired product is a quaternary salt rather than a covalent structure.)

The monoamines generally contain from 1 to about 24 carbon atoms, with 1 to about 12 carbon atoms being preferred, and with 1 to about 6 being more preferred. Examples of monoamines useful in the present invention include methylamine, ethylamine, propylamine, butylamine, octylamine, and dodecylamine. Examples of secondary amines include dimethylamine, diethylamine, dipropylamine, dibutylamine, methylbutylamine, ethylhexylamine, etc. The polyamines may be aliphatic, cycloaliphatic, heterocyclic or aromatic. Examples of the polyamines include alkylene polyamines and heterocyclic polyamines.

Alkylene polyamines are represented by the formula

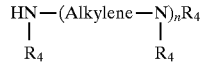

wherein n has an average value between about 1 and about 10, preferably about 2 to about 7 and the "Alkylene" group has from 1 to about 10 carbon atoms, preferably about 2 to about 6. $R_4$ is independently hydrogen or hydrocarbyl, but preferably an aliphatic or hydroxy-substituted aliphatic group of up to about 30 carbon atoms.

Such alkylene polyamines include methylene polyamines, ethylene polyamines, butylene polyamines, propylene polyamines, pentylene polyamines, etc. The higher homologs and related heterocyclic amines such as piperazines and N-amino alkyl-substituted piperazines are also included. Specific examples of such polyamines are ethylene diamine, diethylene triamine (DETA), triethylene tetramine (TETA), tris-(2-aminoethyl)amine, propylene diamine, trimethylene diamine, tripropylene tetramine, tetraethylene pentamine (TEPA), hexaethylene heptamine, pentaethylenehexamine, etc.

Higher homologs obtained by condensing two or more of the above-noted alkylene amines are similarly useful as are mixtures of two or more of the afore-described polyamines.

Ethylene polyamines, such as some of those mentioned above, are useful. Such polyamines are described in detail under the heading "Diamine and Higher Amines, Aliphatic" in Kirk Othmer's "Encyclopedia of Chemical Technology," 4th Edition, Vol. 8, pages 74–108, Wiley Interscience Publishers, New York (1993). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylene polyamines including cyclic condensation products such as piperazines. Ethylene polyamine mixtures are useful.

The amine may also be a heterocyclic polyamine. Among the heterocyclic polyamines are aziridines, azetidines, azolidines, tetra- and dihydropyridines, pyrroles, indoles, piperidines, imidazoles, di- and tetrahydroimidazoles, piperazines, isoindoles, purines, morpholines, thiomorpholines, N-aminoalkylmorpholines, N-aminoalkylthiomorpholines, N-aminoalkylpiperazines, N,N'-diaminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidine, aminoalkyl-substituted piperidines, piperazine, aminoalkyl-substituted piperazines, morpholine, aminoalkyl-substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include N-aminopropylmorpholine, N-aminoethylpiperazine, and N,N'-diaminoethylpiperazine.

Other useful types of polyamine mixtures are those resulting from stripping of the above-described polyamine mixtures to leave as residue what is often termed "polyamine bottoms." In general, alkylene polyamine bottoms can be characterized as having less than 2%, usually less than 1% by weight material boiling below about 200° C. A typical sample of such ethylene polyamine bottoms obtained from the Dow Chemical Company of Freeport, Texas designated "E-100" has a specific gravity at 15.6° C. of 1.0168, a percent nitrogen by weight of 33.15 and a viscosity at 40° C. of 121 centistokes. Gas chromatography analysis of such a sample contains about 0.93% "Light Ends" (most probably DETA), 0.72% TETA. 21.74% tetraethylene pentamine and 76.61% pentaethylene hexamine and higher by weight. These alkylene polyamine bottoms include cyclic condensation products such as piperazine and higher analogs of diethylenetriamine, triethylenetetramine and the like.

Another useful polyamine is a condensation reaction product of at least one hydroxy compound with at least one polyamine reactant containing at least one primary or secondary amino group. The hydroxy compounds are preferably polyhydric alcohols containing from 2 to about 10, preferably 2 to about 6, preferably 2 to about 4 hydroxyl groups and up to 40 aliphatic carbon atoms, preferably from 2 to about 30, more preferably 2 to about 10. The polyhydric alcohols include ethylene glycols, propylene glycols, glycerol, butanediol, hexanediol, sorbitol, arabitol, mannitol, sucrose, fructose, glucose, cyclohexanediol, erythritol, and pentaerythritols. Preferably the hydroxyamine compounds are polyhydric amines, which include any of the above-described monoamines reacted with an alkylene oxide. Examples of polyhydric amines include tri-(hydroxypropyl)amine, tris-(hydroxymethyl) aminomethane, 2-amino-2-methyl-1,3-propanediol, N,N, N'N'-tetrakis(2-hydroxypropyl)ethylenediamine, and N,N, N',N'-tetrakis(2-hydroxyethyl)ethylenediamine, preferably tris(hydroxymethyl)aminomethane (THAM).

Suitable polyamine reactants include triethylenetetramine (TETA), tetraethylenepentamine (TEPA), pentaethylenehexamine (PEHA), and mixtures of polyamines such as the above-described "amine bottoms."

Likewise, in place of an amine, an alcohol can be used to form the reaction product with the triazole and the aldehyde. Suitable alcohols include straight chain and branched alcohols and may include alkyl carbon chains and carbon chains which including aromatic rings or heteratoms such as oxygen or nitrogen. Preferred alcohols are those containing from 3 or especially about 4 to about 24 carbon atoms, including propyl alcohol, butyl alcohol, amyl alcohol, hexyl alcohols such as 4-methyl-2-pentanol, octyl alcohols such as 2-ethylhexanol, and decyl alcohols. Use of alcohols of 6 or more carbon atoms is particularly preferred because such materials impart superior oil solubility to the substituted triazole. Primary alcohols are the most reactive and thus the most suitable for preparation of such products; secondary and tertiary alcohols would be expected to be comparatively unreactive.

A preferred triazole is represented by the formula

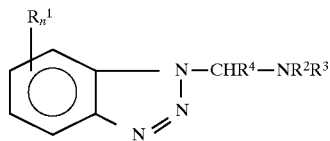

In this formula $R^1$ is a hydrocarbyl group, and n is 0 to 4, provided that if n is greater than 1 not all such hydrocarbyl groups need be identical. Most preferably n=1 and $R^1$ is methyl.

In the above formula $R^2$ and $R^3$ are hydrogen or alkyl, provided that $R^2$ and $R^3$ are not both hydrogen. That is, the $NR^2R^3$ group represents a primary or secondary amine residue, but not ammonia. In a preferred embodiment $R^2$ and $R^3$ are both 2-ethylhexyl, that is, the amine is di-2-ethylhexylamine.

In the above formula $R^4$ is a hydrogen atom or an alkyl group of 1 to about 6 carbon atoms. The $CHR^4$ group corresponds to an aldehyde residue which can be used in the preparation of the preferred material by a condensation process, described below. It is preferred that the aldehyde is formaldehyde or an equivalent form thereof, in which case the $CHR^4$ group is $CH_2$.

The above adduct is prepared by mixing the triazole and the amine in a suitable inert solvent and optionally water, and cooling the mixture in an ice bath. The aldehyde is conveniently added as an aqueous solution in a dropwise manner into the cooled mixture. The mole ratio of triazole: aldehyde:amine is generally 1:1:1. It is generally preferable to use a slight stoichiometric excess (usually about 10% to 20% excess) of the aldehyde and the amine. The reaction is very thermodynamically favorable, particularly when the aldehyde is formaldehyde or paraformaldehyde, and can be run at room temperature or less. However, heating to about 100° C. or higher can be desirable for removal of water of reaction.

Adducts of triazoles, aldehydes and amines are available commercially. For example, the adduct of tolyltriazole:formaldehyde:di-2-ethylhexylamine (1:1:1 m) is available under the designation Irgamet 39 (Ciba-Geigy Corporation).

The detergents are exemplified by oil-soluble neutral and basic salts (i.e. overbased salts) of alkali, alkaline earth, or transition metals with sulfonic acids, carboxylic acids, including hydrocarbyl substituted carboxylic acylating agents, phenols or organic phosphorus acids. The hydrocarbyl-substituted carboxylic acylating agents include agents which have a hydrocarbyl group derived from a polyalkene, such as polybutene. The polyalkenes include homopolymers and inter polymers derived from one or more of the above olefins. The polyalkene is generally characterized as containing from about 8 up to about 300, or from about 30 up to about 200, or from about 35 up to 100 carbon atoms. In one embodiment, the polyalkene is characterized by an $\overline{M}n$ (number average molecular weight) from about 500 to about 5000, or from about 800 to about 2500. In another embodiment Mn varies between about 500 to about 1200 or about 1300. In another embodiment, the hydrocarbyl group is derived from polyalkenes having an $\overline{M}n$ of at least about 1300 up to about 5000, and $\overline{M}w/\overline{M}n$ is from about 1.5 to about 4, preferably from about 1.8 to about 3.6, or from about 2.5 to about 3.2.

The phosphorus acids include those prepared by the treatment of a polyalkene with a phosphorizing agent, such as phosphorus pentasulfide. The most commonly used metals are sodium, potassium, lithium, calcium, and magnesium. The term "basic salt" is used to designate metal salts wherein the metal is present in stoichiometrically larger amounts than the organic acid radical. The overbased salts and borated overbased salts are prepared by means known to those in the art. Patents describing overbased salts, methods of making the salts and components for making the same include U.S. Pat. Nos. 2,501,731; 2,616,911; 2,777,874; 3,384,585; 3,320,162; 3,488,284 and 3,629,109. The disclosure of these patents are hereby incorporated by reference.

The compositions of the invention may also include a dispersant. The dispersants are known in the art. The following are illustrative.

(1) "Carboxylic dispersants" are the reaction products of carboxylic acids (or derivatives thereof) containing at least about 12 carbon atoms, preferably at least about 34 and more preferably at least about 54 carbon atoms and nitrogen containing compounds (such as amine), organic hydroxy compounds (such as phenols and alcohols), and/or basic inorganic materials. These reaction products include imide, amide, and ester reaction products of carboxylic acylating agents. The carboxylic dispersants are generally prepared by reacting one or more of the above described hydrocarbyl substituted carboxylic acylating agent with an amine or hydroxy containing compound, such as an alcohol. Examples of these materials include succinimide dispersants and carboxylic ester dispersants. Examples of these "carboxylic dispersants" are described in British Patent 1,306, 529 and in many U.S. Patents including the following: U.S. Pat. Nos. 3,219,666; 3,316,177; 3,340,281; 3,351,552; 3,381,022; 3,433,744; 3,444,170; 3,467,668; 3,501,405; 3,542,680; 3,576,743; 3,632,511; 4,234,435; and U.S. Pat. Re. 26,433.

(2) "Amine dispersants" are the reaction products of relatively high molecular weight aliphatic or alicyclic halides and amines, preferably polyalkylene polyamines. These dispersants are described above as polyalkene-substituted amines. Examples thereof are described for example, in the following U.S. Pat. Nos. 3,275,554; 3,438,757; 3,454,555; and 3,565,804.

(3) "Mannich dispersants" are the reaction products of alkylphenols and aldehydes (especially formaldehyde) and amines (especially amine condensates and polyalkylenepolyamines). The materials described in the following U.S. Patents are illustrative: U.S. Pat. Nos. 3,036,003; 3,236,770; 3,414,347; 3,448,047; 3,461,172; 3,539,633; 3,586,629; 3,591,598; 3,634,515; 3,725,480; 3,726,882; and 3,980,569.

(4) "Post-treated dispersants" are the products obtained by post-treating the carboxylic, amine or Mannich dispersants with reagents such as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos. 3,200,107; 3,282,955; 3,367,943; 3,513,093; 3,639,242; 3,649,659; 3,442,808; 3,455,832; 3,579,450; 3,600,372; 3,702,757; and 3,708,422.

(5) "Polymeric dispersants" are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. Polymeric dispersants include esters of styrene-maleic anhydride copolymers. Examples thereof are disclosed in the following U.S. Pat. Nos. 3,329,658; 3,449,250; 3,519,656; 3,666,730; 3,687,849; and 3,702,300.

The above-noted patents are incorporated by reference herein for their disclosures of dispersants.

Other antiwear, extreme-pressure, friction modifiers and corrosion-inhibiting agents include chlorinated aliphatic hydrocarbons, such as chlorinated wax; alkyl-substituted succinic acids or anhydrides reacted with alkylene oxides such as ethylene oxide or propylene oxide; sulfurized alkylphenols; phosphosulfurized hydrocarbons, such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; boron-containing compounds including borate esters; dimercaptothiadiazole derivatives; amino-mercaptothiadiazole derivatives; and molybdenum compounds. Many of the above-mentioned antioxidants also serve as extreme-pressure agents and corrosion-inhibitors.

Pour point depressants are an additive often included in the lubricating oils described herein. Examples of useful pour point depressants are polymethacrylates; polyacrylates; polyacrylamides; condensation products of haloparaffin waxes and aromatic compounds; vinyl carboxylate polymers; styrene-maleic anhydride copolymer esters; and polymers of dialkylfumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Antifoam agents are used to reduce or prevent the formation of stable foam. Typical antifoam agents include silicones or organic polymers. Additional antifoam compositions are described in "Foam Control Agents", by Henry T. Kerner (Noyes Data Corporation, 1976), pages 125–162.

Viscosity-improvers include but are not limited to polyisobutenes, polymethacrylate acid esters, polyacrylate acid esters, diene polymers, polyalkyl styrenes, alkenyl aryl conjugated diene copolymers (preferably styrene-maleic anhydride copolymer esters), polyolefins, hydrogenated isoprenoids and multi-functional viscosity improvers.

The following examples illustrate some of the compositions of this invention.

|  | %/wt |
| --- | --- |
| Example A | |
| Polyol ester of Example 1 | 98 |
| 2,6-di-t-butylphenol (DTBP) | 2 |
| Example B | |
| Polyol ester of Example 2 | 98 |
| 2,6-di-t-butylphenol | 2 |
| Example C | |
| Polyol ester of Example 1 | 97.95 |
| 2,6-di-t-butylphenol | 2 |
| Irgamet 39 | 0.05 |
| Example D | |
| Polyol ester of Example 2 | 97.95 |
| 2,6-di-t-butylphenol | 2 |
| Irgamet 39 | 0.05 |
| Example E | |
| Polyol ester of Example 4 | 98 |
| Substituted phenothiazine of Example AO-9 | 2 |
| Example F | |
| Polyol ester of Example 4 | 97.9 |
| 2,2'-bis(6-t-butyl-4-heptylphenol) | 2 |
| Tolyltriazole | 0.1 |
| Example G | |
| Polyol ester of Example 5 | 98 |
| 2-methyl-6-t-butyl-4-heptylphenol | 2 |

The compositions of the present invention comprising the polyol esters described above and at least one antioxidant (e.g., Examples A, B, E and G), and the compositions comprising the polyol esters described above, at least one antioxidant and at least one metal deactivator (e.g., Examples C, D and F) exhibit improved oxidative stability. The oxidative stability of the compositions of the invention are determined in the "Rotary Bomb Oxidation Test" (RBOT; ASTM D-2272). For comparison, a commercial trimethylolpropanoyl trioleate (Emery® 2964) in which the trioleate is prepared from an acid mixture containing 65.75% of oleic acid also is subjected to the Rotary Bomb Oxidation Test. Typical results of these tests are summarized in Table II.

TABLE II

RBOT Results

|  | Time (min) for a 25-lb pressure loss |
| --- | --- |
| Emery 2964 (A) | 10 |
| Polyol ester of Example 1 (B) | 11 |

TABLE II-continued

RBOT Results

|  | Time (min) for a 25-lb pressure loss |
| --- | --- |
| Polyol ester of Example 2 (C) | 15 |
| — | |
| A + 2% DTBP | 100 |
| B + 2% DTBP | 172 |
| C + 2% DTBP | 318 |
| — | |
| A + 2% DTBP + Irgamet 39 | 113 |
| B + 2% DTBP + Irgamet 39 | 348 |
| C + 2% DTBP + Irgamet 39 | 559 |

As can be seen from the results in Table II, mixtures of the TMP trioleates of the invention with antioxidant have significantly better oxidative stability than a mixture Emery 2964 and the same antioxidant. The mixtures of TMP trioleates of the invention with antioxidant and metal deactivator have an even greater oxidative stability than Emery 2964 with the same antioxidant and metal deactivator.

The compositions of the present invention which comprise (A) a polyol ester as described above;

(B) at least one antioxidant may comprise from about 95% to 99.9% by weight of the polyester polyol and from about 0.1% to about 5% by weight of the antioxidant. When the compositions of the present invention also contain at least one of the performance additive compositions (C) described above, the compositions generally comprise (A) from about 75% by weight to about 99.89% by weight of the polyester polyol (A);

(B) from about 0.1% by weight to about 5% by weight of the antioxidant; and (C) from about 0.01% by weight to about 20% by weight of at least one of the performance additive compositions described above.

Lubricants.

As previously indicated, the polyol esters of the present invention are useful in preparing lubricants, particularly lubricants based on synthetic lubricating oils and mixtures thereof. The compositions of the invention can be employed in a variety of lubricants based on diverse oils of lubricating viscosity, including natural and other synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. The lubricants can also be used in natural gas engines, stationary power engines and turbines and the like. Automatic or manual transmission fluids, transaxle lubricants, gear lubricants, both for open and enclosed systems, tractor lubricants, metal-working lubricants, hydraulic fluids and other lubricating oil and grease compositions also can be prepared with the compositions of the present invention. The polyester polyols may also be used in lubricants for wirerope, walking cam, slideway, rock drill, chain and conveyor belt, worm gear, bearing, and rail and flange applications.

The lubricating oil compositions of the present invention may comprise a polyol ester (A) as described above and at least one other oil of lubricating viscosity which is different from the ester (A). Such lubricating oil compositions may comprise from about 10% to about 95% or more by weight of the polyol ester (A) and from about 0.5% to about 90% by weight of an oil of lubricating viscosity other than the ester (A). Such lubricating oil compositions also may, and preferably, contain at least one antioxidant and other performance additives as described above. The amount of the antioxidant and other performance additives included in the lubricating oil composition may each be in the range of from about 0.01% to about 10%, more often from about 0.1% to about 7% or 8%. The amount of the antioxidant in other performance additives included in the lubricating oil compositions will depend upon the use for which the lubricant is designed, and such amounts can be readily determined by those skilled in the art.

In another embodiment, the lubricating oil compositions of the present invention comprise (A) from about 1% by weight to about 98.89% by weight of the polyol ester (A);

(B) from about 0.01% by weight to about 5% by weight of at least one antioxidant;

(C) from about 1% to about 74% by weight of an oil of lubricating viscosity other than the polyol ester of (A); and (D) from about 0.1% to about 20% of at least one additive composition selected from the group consisting of detergents, dispersants, metal deactivators, antiwear agents, extreme-pressure agents, viscosity-index improvers, pour point depressants, foam inhibitors, demulsifiers, friction modifiers, and corrosion-inhibitors.

The lubricating compositions and methods of this invention employ an oil of lubricating viscosity other than the polyol esters (A) described above, and such oils include natural or synthetic lubricating oils and mixtures thereof. Natural oils include animal oils, vegetable oils (including high oleic vegetable oils), products derived from vegetable oils, (e.g., rapeseed oil reacted with methanol in the presence of a catalyst forms a rapeseed methyl ester), mineral lubricating oils, solvent or acid treated mineral oils, hydro-refined mineral oil and hydro-cracked mineral oils. Synthetic lubricating oils include hydrocarbon oils (poly-alpha-olefins), halo-substituted hydrocarbon oils, alkylene oxide polymers, esters of mono- and dicarboxylic acids and polyols, esters of phosphorus-containing acids, polymeric tetrahydrofurans and silicon-based oils. Unrefined, refined, and rerefined oils, either natural or synthetic, may be used in the compositions of the present invention. A description of oils of lubricating viscosity occurs in U.S. Pat. No. 4,582,618 (column 2, line 37 through column 3, line 63, inclusive), herein incorporated by reference for its disclosure to oils of lubricating viscosity.

The oil of lubricating viscosity also may comprise high oleic vegetable oils such as the oils described above which may be used as sources of high oleic acid mixtures. Examples of high oleic vegetable oils useful as the oil of lubricating viscosity include high oleic safflower oil, high oleic peanut oil, high oleic corn oil, high oleic olive oil, high oleic rapeseed oil, canola oil, high oleic soybean oil, high oleic cottonseed oil, high oleic lesquerella oil, and high oleic palm oil. A preferred high oleic vegetable oil is high oleic sunflower oil obtained from *Helianthus sp*. This product is available from SVO Enterprises, Eastlake, Ohio as Sunyl® high oleic sunflower oil. Sunyl® 80 oil is a high oleic triglyceride wherein the acid moieties comprise from about 77% to about 81% of oleic acid. Sunyl® 90 oil is another high oleic triglyceride wherein the acid moieties comprise from about 86% to 92% oleic acid. Another useful high oleic vegetable oil is high oleic rapeseed oil obtained from *Brassica campestris* or *Brassica napus*, also available from SVO Enterprises as RS high oleic rapeseed oil. RS 80 signifies a rapeseed oil wherein the acid moieties comprise about 80% of oleic acid.

In one embodiment, the oil of lubricating viscosity or a mixture of oils of lubricating viscosity are selected to provide lubricating compositions with a kinematic viscosity of at least about 1.8 cSt, or at least about 4.0 cSt at 100° C. In one embodiment, the lubricating compositions have an SAE gear viscosity number of at least about SAE 65, more preferably at least about SAE 75. The lubricating composition may also have a so-called multigrade rating such as SAE 75W-80, 75W-90, or 80W-90. Multigrade lubricants may include a viscosity improver which is formulated with the oil of lubricating viscosity to provide the above lubricant grades. Useful viscosity improvers include but are not limited to polyolefins, such as ethylene-propylene copolymers, or polybutylene rubbers, including hydrogenated rubbers, such as styrene-butadiene or styrene-isoprene rubbers; or polyacrylates, including polymethacrylates. Preferably the viscosity improver is a polyolefin or polymethacrylate, more preferably polymethacrylate. Viscosity improvers available commercially include Acryloid™ viscosity improvers available from Rohm & Haas; Shellvis™ rubbers available from Shell Chemical; hydrogenated polyisoprenoids from Kurary Co.; and Lubrizol 3174 available from The Lubrizol Corporation.

In another embodiment, the oil of lubricating viscosity is selected to provide lubricating compositions for crankcase applications, such as for gasoline and diesel engines. Typically, the lubricating compositions are selected to provide an SAE crankcase viscosity number of 10W, 20W, or 30W lubricants. The lubricating composition may also have a so called multi-grade rating such as SAE 5W-30, 10W-30, 10W40, 20W-50, etc. As described above, multi-grade lubricants include a viscosity improver which is formulated with the oil of lubricating viscosity to provide the above lubricant grades.

The following examples relate to lubricating compositions containing the polyol esters of the present invention.

EXAMPLE L-1

A lubricant is prepared by incorporating 2% by weight of 2,6-di-t-butyl phenol into 98% by weight of the polyol ester of Example 1.

EXAMPLES L-2 TO L-7

Examples L-2 to L-7 are examples of lubricants of the invention useful as hydraulic fluids. The formulations for these fluids are summarized in the following Table III.

TABLE III

Hydraulic Fluids

| | L-2 | L-3 | L-4 | L-5 | L-6 | L-7 |
|---|---|---|---|---|---|---|
| Polyol ester of Example 1 | 96 | — | — | 98.75 | — | — |
| Polyol ester of Example 2 | — | — | 38 | — | — | 79 |
| Polyol ester of Example 4 | — | 96 | — | — | 98.75 | — |
| Sunyl ® 80 | — | — | 58 | — | — | 19.75 |
| 2,6-di-t-butylphenol | 0.53 | 0.53 | 0.53 | 0.32 | 0.32 | 0.32 |
| Dinonyldiphenylamine | 0.53 | 0.53 | 0.53 | 0.32 | 0.32 | 0.32 |
| Reaction product of dialkyl-phosphorodithioic acid with methyl acrylate and an alkylene oxide | 0.66 | 0.66 | 0.66 | 0.42 | 0.42 | 0.42 |

TABLE III-continued

Hydraulic Fluids

| | L-2 | L-3 | L-4 | L-5 | L-6 | L-7 |
|---|---|---|---|---|---|---|
| Alkylsuccinic anhydride reacted with PrO | 0.10 | 0.10 | 0.10 | 0.06 | 0.06 | 0.06 |
| Tolyltriazole | 0.05 | 0.05 | 0.05 | 0.03 | 0.03 | 0.03 |
| Ethylene oxide-propylene oxide copolymer | 0.01 | 0.01 | 0.01 | 0.006 | 0.006 | 0.006 |
| Maleic anhydride-styrene copolymer ester; pour point depressant | 2 | 2 | 2 | — | — | — |
| Mineral oil | 0.12 | 0.12 | 0.12 | 0.094 | 0.094 | 0.094 |

EXAMPLES L-8 TO L-10

These examples illustrate lubricants of the invention useful as two-cycle oils. The formulations are summarized in the following Table IV.

TABLE IV

Two Cycle Oils

| | L-8 | L-9 | L-10 |
|---|---|---|---|
| Polyol ester of Example 1 | 28 | — | 41.5 |
| Polyol ester of Example 2 | — | 27 | — |
| Sunyl ® 80 | 55 | 25 | 41.5 |
| 4-polybutenyl-2-aminophenol | 10.95 | 9.49 | 7.5 |
| Polybutenyl succinic anhydride reacted with tetraethylene pentamine | 2.55 | 2.21 | — |
| Isostearic acid reacted with tetraethylene pentamine | 1.28 | 1.11 | 7.5 |
| Dinonyldiphenylamine | 0.22 | 0.19 | — |
| Maleic anhydride-styrene copolymer ester; pour point depressant | 2 | 1 | 2 |
| Biodegradable mineral oil | — | 34 | — |

EXAMPLES L-11 TO L-15

The examples in Table V illustrate lubricants of the present invention which are useful as gear oils.

TABLE V

Gear Oils

| | L-11 | L-12 | L-13 | L-14 | L-15 |
|---|---|---|---|---|---|
| Polyol ester of Example 1 | 39 | — | — | — | — |
| Polyol ester of Example 2 | — | 41.5 | — | 50 | — |
| Polyol ester of Example 4 | — | — | 53 | — | 60 |
| Sunyl ® 80 | 39 | 41.5 | 30 | 43 | — |
| Rapeseed oil | — | — | — | — | 32.25 |
| Dibutylpolysulfide | 3.2 | 3.2 | 3.2 | — | — |
| Sulfurized isobutylene | — | — | — | 0.78 | 0.68 |
| Mixture of mono- and diesters of phosphoric acid, alkylamine salt | 1.20 | 1.20 | 1.20 | 0.46 | 0.40 |
| Polyisobutenyl succinic anhydride reacted with EPA and boric acid | 0.90 | 0.90 | 0.90 | — | — |
| Polyisobutenyl succinic anhydride reacted with TEPA | — | — | — | 0.05 | 0.04 |
| Heptylhydroxyphenyl thio-substituted 1,3,4-thiadiazole | 0.09 | 0.09 | 0.09 | — | — |
| 9-octadecenamide | 0.09 | 0.09 | 0.09 | — | — |
| Alkyl acrylate polymer | 0.07 | 0.07 | 0.07 | 0.02 | 0.02 |
| Monoisopropanolamine | 0.03 | 0.03 | 0.03 | — | — |
| Alkylthiadiazole | 0.03 | 0.03 | 0.03 | — | — |
| Maleic anhydride-styrene copolymer ester | 15.0 | — | 10 | 5 | 6 |
| Acryloid ® 1267 | — | 10 | — | — | — |

TABLE V-continued

Gear Oils

|  | L-11 | L-12 | L-13 | L-14 | L-15 |
|---|---|---|---|---|---|
| Soybean oil | — | — | — | 0.29 | 0.25 |
| N-oleyl-1,3-propanediamine | — | — | — | 0.06 | 005 |
| Tolyltriazole | — | — | — | 0.02 | 0.02 |
| Ethylene oxide-proplene oxide copolymer | — | — | — | 0.04 | 0.03 |
| Mineral oil | 1.39 | 1.39 | 1.39 | 0.28 | 0.26 |

EXAMPLES L-16 TO L-17

These examples illustrate lubricants of the present invention which are useful in ATF applications.

TABLE VI

ATF

|  | L-16 | L-17 |
|---|---|---|
| Polyol ester of Example 1 | 91 | — |
| Polyol ester of Example 2 | — | 51.5 |
| Sunyl ® 80 | — | 40.0 |
| Maleic anhydride-styrene copolymer ester; pour point depressant | 3.0 | 2.5 |
| Reaction product of polyisobutenyl succinic anhydride with TEPA and post-treated with $CS_2$ | 2.0 | 2.0 |
| Polyisobutenyl succinic anhydride reacted with TEPA and boric acid | 1.0 | 1.0 |
| Hydroxythioether of t-dodecyl mercaptan and propylene oxide | 0.5 | 0.5 |
| Dinonyldiphenylamine | 0.5 | 0.5 |
| Ethoxylated tallow amine | 0.05 | 0.05 |
| Dibutyl phosphite | 0.06 | 0.06 |
| Zinc oleate | 0.08 | 0.08 |
| Sulfurized soybean oil | 0.27 | 0.27 |
| Basic calcium sulfonate | 0.97 | 0.97 |
| Phosphoric acid (85%) | 0.03 | 0.03 |
| Polydimethylsiloxane | 0.002 | 0.002 |
| Mineral oil | 0.54 | 0.54 |

When the lubricant is to be used in the form of a grease, various quantities of thickeners and other additive components are incorporated into the lubricant to provide desirable properties. A wide variety of thickeners can be used in the preparation of the greases of this invention. The thickener is employed in an amount from about 0.5 to about 30 percent, and preferably from 3 to about 15 percent by weight of the total grease composition. Including among the thickeners are alkali and alkaline earth metal soaps of fatty acids and fatty materials having from about 12 to about 30 carbon atoms. The metals are typified by sodium, lithium, calcium and barium. Examples of fatty materials include stearic acid, hydroxystearic acid, stearin, oleic acid, palmitic acid, myristic acid, cottonseed oil acids, and hydrogenated fish oils.

Other thickeners include salt and salt-soap complexes, such as calcium stearate-acetate (U.S. Pat. No. 2,197,263), barium stearate-acetate (U.S. Pat. No. 2,564,561), calcium stearate-caprylate-acetate complexes (U.S. Pat. No. 2,999,066), calcium salts and soaps of low-intermediate and high-molecular weight acids and of nut oil acids, aluminum stearate, and aluminum complex thickeners. Useful thickeners include hydrophilic clays which are treated with an ammonium compound to render them hydrophobic. Typical ammonium compounds are tetraalkyl ammonium chlorides. These clays are generally crystalline complex silicates. These clays include bentonite, attapulgite, hectorite, illite, saponite, sepiolite, biotite, vermiculite, zeolite clays and the like.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A composition comprising:

a polyol ester derived from (A) an aliphatic or alicyclic polyol containing from 2 to about 10 hydroxyl groups and (B) an aliphatic monocarboxylic acid mixture derived from a high oleic vegetable oil wherein the oleic content is at least 72 percent and the vegetable oil is canola oil, sunflower oil or peanut oil; with at least one antioxidant selected from the group consisting of phenolics, aromatic amines and tocophenols and at least one metal deactivator selected from the group consisting of benzotriazole and benzotriazole derivatives and wherein all the hydroxyl groups of the polyol are esterified with the acid mixture.

2. The composition of claim 1 wherein the polyol is an aliphatic polyol containing from 2 to about 20 carbon atoms.

3. The composition of claim 1 wherein the polyol (A) is an aliphatic polyol and is characterized by the formula

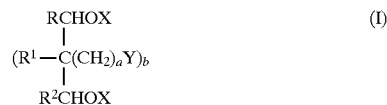

wherein each X independently is hydrogen, a hydroxyhydrocarbyl or a hydroxyhydrocarbyloxyhydrocarbyl group, R, $R^1$ and $R^2$ are each independently hydrogen, hydrocarbyl, hydroxyhydrocarbyl or alkoxyhydrocarbyl groups, and a and b are each independently integers from 0 to about 6, Y is hydrogen or hydroxyl, or b is 1 and Y is

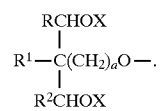

4. The composition of claim 3 wherein R and $R^2$ are hydrogen, Y is a hydroxyl group, and a is 0 or 1.

5. The composition of claim 3 wherein R and $R^2$ are hydrogen, $R^1$ is hydrogen or an alkyl group, Y is a hydroxyl group and a is 0.

6. The composition of claim 3 wherein R and $R^2$ are each independently hydrogen or alkyl groups, and b is 0.

7. The composition of claim 3 wherein the polyol (A) is selected from the group consisting of 1,3-propanediol, 2,3-butanediol, 2-ethyl-2-butyl-1,3-propanediol, neopentyl glycol, 2,2,4-trimethyl-1,3-pentanediol, trimethylolpropane, pentaerythritol, ditrimethylolpropane, dipentaerythritol and sorbitol.

8. The composition of claim 1 wherein the polyol (A) is an aliphatic polyol characterized by the formula

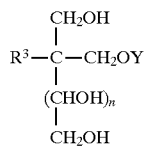

(II)

wherein R³ is an alkyl group containing from 1 to about 6 carbon atoms or a hydroxymethyl group, Y is hydrogen or

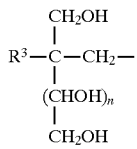

and n is an integer of from 0 to about 6.

9. The composition of claim 8 wherein n=0.

10. The composition of claim 8 wherein R³ is an alkyl group containing from 1 to about 6 carbon atoms and n=0.

11. The composition of claim 8 wherein R³ is an ethyl group, Y is H, and n=0.

12. The composition of claim 8 wherein R³ is a hydroxymethyl group, Y is H, and n=0.

13. The composition of claim 1 wherein the polyol (A) is an alicyclic polyol containing from 5 to about 10 carbon atoms and 5 to 10 hydroxyl groups.

14. The composition of claim 13 wherein the polyol (A) is inositol.

15. The composition of claim 1 wherein the acid mixture of (B) comprises from about 75% to about 95% by weight of oleic acid.

16. The composition of claim 1 wherein the acid mixture (B) comprises at least about 78% by weight of oleic acid.

17. The composition of claim 1 wherein the acid mixture of (B) comprises at least about 75% by weight of oleic acid and the weight ratio of linoleic acid to oleic acid in the mixture is less than about 0.20.

18. The composition of claim 1 wherein the acid mixture (B) comprises at least about 78% by weight of oleic acid, and the ratio of linoleic acid to oleic acid in the mixture is less than about 0.16

19. The composition of claim 1 wherein the acid mixture of (B) comprises at least about 85% by weight of oleic acid and the weight ratio of linoleic acid to oleic acid in the mixture is less than about 0.12.

20. The composition of claim 1 wherein the acid mixture of (B) comprises at least about 90% by weight of oleic acid and the weight ratio of linoleic acid to oleic acid in the mixture is less than about 0.08.

21. The composition of claim 1 wherein the acid mixture (B) comprises at least about 72% by weight of oleic acid and less than 5% by weight of linolenic acid.

22. The composition of claim 1 wherein the antioxidant is selected from phenolic and arylamine antioxidants.

23. The composition of claim 1 wherein the antioxidant is characterized by the formula

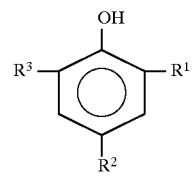

wherein R¹ is hydrogen or an alkyl group containing from 1 to 9 carbon atoms, R² is hydrogen or an alkyl or alkoxy group, and R³ is an alkyl group containing from 1 to about 9 carbon atoms.

24. The composition of claim 1 also containing:

(C) at least one additive composition selected from the group consisting of detergents, dispersants, metal deactivators, antiwear agents, extreme pressure agents, viscosity index modifiers, pour point depressants, foam inhibitors, demulsifiers, friction modifiers and corrosion inhibitors.

25. The composition of claim 24 comprising:

from about 75% by weight to about 99.89% by weight of the polyol ester;

from about 0.1% by weight to about 5% by weight of the antioxidant; and from about 0.01% by weight to about 20% by weight of at least one additive composition selected from the group consisting of detergents, dispersants, metal deactivators, antiwear agents, extreme pressure agents, viscosity index modifiers, pour point depressants, foam inhibitors, demulsifiers, friction modifiers and corrosion inhibitors.

26. The composition of claim 1 wherein the antioxidant is 2,6-di-t-butylphenol, dinonyldiphenylamine, or mixtures thereof, and the metal deactivator (C) is tolyltriazole or nonylbenzotriazole.

27. The composition of claim 1 wherein the antioxidant is a phenolic comprising nonylbenzotriazole.

28. A lubricating oil composition comprising:

the polyol ester of claim 1; and an oil of lubricating viscosity other than the polyol ester.

29. The lubricating oil composition of claim 28 comprising:

from about 1% by weight to about 98.89% by weight of the polyol ester;

from about 0.01% by weight to about 5% weight of at least one antioxidant;

from about 1% by weight to about 74% by weight of the oil of lubricating viscosity other than a polyol ester; and from about 0.1% to about 20% of at least one additive composition selected from the group consisting of detergents, dispersants, metal deactivators, antiwear agents, extreme pressure agents, viscosity index modifiers, pour point depressants, foam inhibitors, demulsifiers, friction modifiers and corrosion inhibitors.

* * * * *